(12) United States Patent
Lee et al.

(10) Patent No.: US 11,679,205 B2
(45) Date of Patent: Jun. 20, 2023

(54) HIGH PRECISION SYRINGE WITH REMOVABLE PUMP UNIT

(71) Applicant: Zyno Medical, LLC, Natick, MA (US)

(72) Inventors: Chao Young Lee, Weston, MA (US);
Zhenhua Mao, Andover, MA (US);
Mei Zhang, Sharon, MA (US);
Frederick Lee, Boston, MA (US)

(73) Assignee: Zyno Medical LLC, Natick, MA (US)

( * ) Notice: Subject to any disclaimer, the term of this patent is extended or adjusted under 35 U.S.C. 154(b) by 210 days.

(21) Appl. No.: 16/814,008

(22) Filed: Mar. 10, 2020

(65) Prior Publication Data

US 2020/0238018 A1    Jul. 30, 2020

Related U.S. Application Data

(63) Continuation-in-part of application No. 16/509,701, filed on Jul. 12, 2019.
(Continued)

(51) Int. Cl.
*A61M 5/315*  (2006.01)
*A61M 5/145*  (2006.01)
(Continued)

(52) U.S. Cl.
CPC ...... *A61M 5/31556* (2013.01); *A61M 5/1456* (2013.01); *A61M 5/172* (2013.01);
(Continued)

(58) Field of Classification Search
CPC .............. A61M 5/1452; A61M 5/1456; A61M 5/14566; A61M 5/14546;
(Continued)

(56) References Cited

U.S. PATENT DOCUMENTS 5,902,276 A * 5/1999 Namey, Jr. ......... A61M 5/31511
604/218
5,947,929 A * 9/1999 Trull ................. A61M 5/14546
604/152
(Continued)

FOREIGN PATENT DOCUMENTS

EP    1 323 441    7/2003
EP    2 510 960    10/2012
(Continued)

*Primary Examiner* — Emily L Schmidt
(74) *Attorney, Agent, or Firm* — Boyle Fredrickson S.C.

(57) ABSTRACT

A digital syringe is used with conventional polymer disposable syringe construction to be practical in the medical environment. Errors associated with the larger volumes of the syringes (which exacerbate minor errors in plunger position) and the flexibility and dimensional variations of the polymer plungers are accommodated by direct measurement of the syringe plunger position rather than indirect measurement of motor position and inference of syringe plunger position. This direct measurement eliminates mechanical tolerances ("stack up") in the motor, gear train, and lead screw on plunger movement, an effect exacerbated by flexibility of the plunger and changes in syringe resistance and medicament viscosity, for example, with different medicaments or when the syringe is refrigerated. The digital syringe may be combined with the motor unit to provide additional versatility.

17 Claims, 11 Drawing Sheets

Related U.S. Application Data

(60) Provisional application No. 62/799,475, filed on Jan. 31, 2019, provisional application No. 62/697,632, filed on Jul. 13, 2018.

(51) Int. Cl.
  *A61M 5/172* (2006.01)
  *A61M 5/31* (2006.01)

(52) U.S. Cl.
  CPC ........ *A61M 5/3137* (2013.01); *A61M 5/3158* (2013.01); *A61M 5/31505* (2013.01); *A61M 5/31515* (2013.01); *A61M 5/31546* (2013.01); *A61M 2205/3331* (2013.01)

(58) Field of Classification Search
  CPC ......... A61M 2005/14553; A61M 2005/14573; A61M 5/1458; A61M 5/31515
  See application file for complete search history.

(56) References Cited

U.S. PATENT DOCUMENTS

| | | | | |
|---|---|---|---|---|
| 6,676,642 B2 * | 1/2004 | Beebe | ............... | A61M 5/31513 604/228 |
| 8,911,403 B2 | 12/2014 | Flachbart et al. | | |
| 2007/0093752 A1 | 4/2007 | Zhao et al. | | |
| 2008/0082055 A1 * | 4/2008 | Lloyd | ............... | A61M 5/31515 604/218 |
| 2009/0171291 A1 | 7/2009 | Bente, IV et al. | | |
| 2010/0057014 A1 * | 3/2010 | Cane | ................. | A61M 5/31515 604/222 |
| 2010/0274180 A1 | 10/2010 | Donovan et al. | | |
| 2014/0188076 A1 * | 7/2014 | Kamen | ............. | A61M 5/16831 604/506 |
| 2015/0379900 A1 | 12/2015 | Samosky et al. | | |
| 2016/0166761 A1 * | 6/2016 | Piehl | .................. | A61M 5/1408 604/506 |
| 2020/0016331 A1 | 1/2020 | Lee | | |

FOREIGN PATENT DOCUMENTS

| | | | |
|---|---|---|---|
| EP | 3 222 308 | 9/2017 | |
| JP | 2001522660 | 11/2001 | |
| JP | 2010518975 | 6/2010 | |
| KR | 100578288 | 5/2006 | |
| WO | 9822168 | 5/1998 | |
| WO | WO 2017/108686 * | 6/2017 | .......... A61M 5/1456 |

* cited by examiner

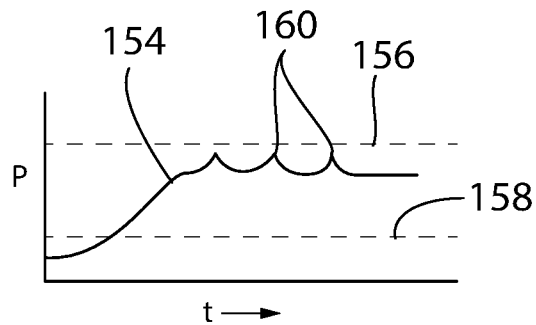
Fig. 10
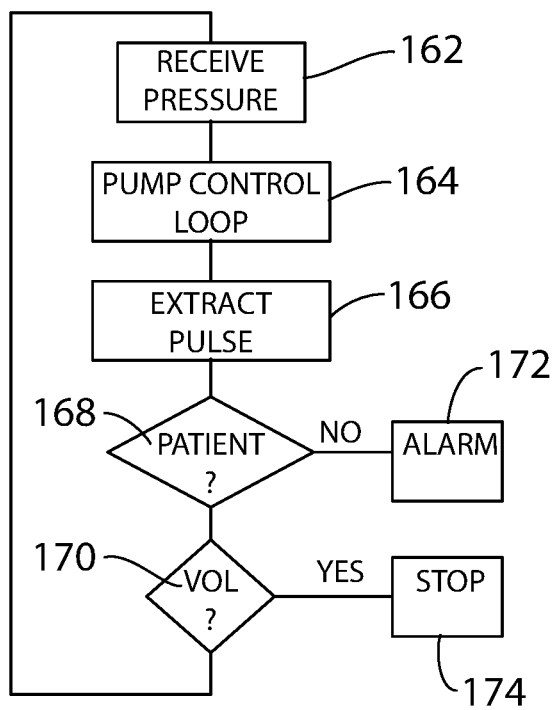
Fig. 11
Fig. 12
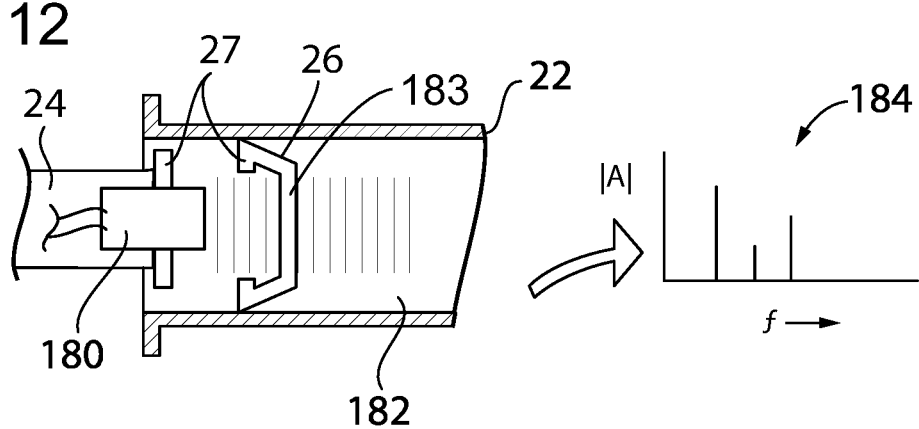

HIGH PRECISION SYRINGE WITH REMOVABLE PUMP UNIT

CROSS REFERENCE TO RELATED APPLICATION

This application is a continuation-in-part of U.S. patent application Ser. No. 16/509,701, filed Jul. 12, 2019, which claims the benefit of U.S. Provisional Application No. 62/697,632, filed Jul. 13, 2018, and U.S. Provisional Application No. 62/799,475, filed Jan. 31, 2019, each of which are hereby incorporated by reference.

BACKGROUND OF THE INVENTION

The present invention relates to syringes as used for medical purposes, and in particular, to a syringe that provides improved precision.

Syringes are known for administering medicaments, such as medicine or contrast agents, to a patient over a period of time. Such syringes include a plunger sliding in a syringe tube. The plunger includes a piston-like seal that fits tightly against the inner surface of the syringe tube. Movement of the plunger decreases the volume contained in the syringe tube between the plunger seal and an outlet of the syringe tube to provide a positive displacement pumping action.

Control of the delivery of medicine using a syringe is provided by gradations printed on the syringe tube. Such gradations can be difficult to read or interpret and require the healthcare professional to remember a starting position and calculate an ending position of the syringe on the gradations when a given dose is required.

"Digital syringes" exist for use in the laboratory and eliminate many of the problems of accurately reading a syringe. Such digital syringes combine a high precision small-volume syringe, providing a high accuracy glass tube, with an instrumented operator that may be pressed by the user to move the plunger while measuring that operator movement electronically for display on a digital gauge. The syringe plunger may have a special coupling to attach to the operator to eliminate any looseness and error and may be fabricated out of precision metal components. Such syringes are intended to be cleaned and reused, impractical in the medical environment for reasons of cost, sterility, and cross-contamination of drugs.

SUMMARY OF THE INVENTION

The present invention provides a digital syringe that can be used with conventional polymer disposable syringe construction to be practical in the medical environment. Errors associated with the larger volumes of the syringes (which exacerbate minor errors in plunger position) and the flexibility and dimensional variations of the polymer plungers are by direct measurement of the syringe plunger position rather than indirect measurement of motor position and inference of syringe plunger position. This direct measurement eliminates mechanical tolerances ("stack up") in the motor, gear train, and lead screw on plunger movement, an effect exacerbated by flexibility of the plunger and changes in syringe resistance and medicament viscosity, for example, with different medicaments or when the syringe is refrigerated. The digital syringe may be combined with the motor unit to provide additional versatility.

Specifically, in one embodiment, the present invention provides a sensor system for a measured delivery of a liquid medicament from a syringe of a type having a tubular barrel terminating at a needle adapter and including a closely fitting plunger activated elastomeric piston, the sensor system having a housing receiving removably receiving the tubular barrel to extend along an axis from the housing; a plunger slidably received to move along the axis within the housing corresponding with motion of the elastomeric piston; and an electronic sensor attached to and stationary with respect to the housing and sensing a sensor element to provide direct measurement of motion of the plunger along the axis with respect to the housing to provide an electronic signal indicating movement of the plunger.

It is thus a feature of at least one embodiment of to provide a medical syringe providing direct digital readout of plunger position thereby allowing the use of standard disposable syringes.

A portion of the plunger may extend out of the housing for manual operation of the syringe by pressing on the plunger portion.

It is thus a feature of at least one embodiment of the present invention to permit manual operation of the syringe while still providing cumulative measurement of an amount of drug delivered.

The housing may provide outwardly extending flanges engaging with the user's fingers to assist with pressing on the plunger portion.

It is thus a feature of at least one embodiment of the present invention to facilitate manual pressing of the plunger against the attached tubular barrel and elastomeric piston.

A knob may rotate a driver in rolling contact with a surface of the plunger along the axis to move the plunger with rotation of the driver.

It is thus a feature of at least one embodiment of the present invention to permit finely controlled movement of the plunger to deliver precise amounts of liquid medicament without a motor.

A display may be supported by the housing and may communicate with the sensor to display an indication of displacement of the elastomeric piston.

It is thus a feature of at least one embodiment of the present invention to provide an easy to understand display of dispensed volume medical professional.

The display may provide units of volume based on a predetermined dimension of a cross-section of the tubular barrel.

It is thus a feature of at least one embodiment of the present invention to provide useful volume change information to the medical professional so that delivery can be controlled over time and volume remaining to be delivered can be ascertained.

A motor unit may engage the plunger to move the plunger with motion of the motor.

It is thus a feature of at least one embodiment of the present invention to provide automatic liquid medicament delivery for precise delivery without human interaction which introduces human error and risk of drug diversion.

A controller may execute a stored program stored in memory to: receive a command signal indicating a desired amount of displacement of the syringe plunger based on a desired delivery rate; receive a displacement signal indicating an actual amount of displacement of the syringe plunger; and compare the displacement signal with the command signal to produce an error signal indicating a difference between the command signal and the displacement signal. The motor unit may communicate with the controller to control an electrical motor based on the error signal.

It is thus a feature of at least one embodiment of the present invention to provide a feedback control system allowing the motor to operate automatically to eliminate mechanical tolerance stack up.

The housing may releasably receive the motor unit. The motor unit may include a self-contained battery.

It is thus a feature of at least one embodiment of the present invention to allow the sensor unit to be easily interchange between manual administration of drugs and automatic operation of the motor unit.

The housing may further include electrical connectors that connect the motor unit and the housing when the motor unit is received by the housing.

It is thus a feature of at least one embodiment of the present invention to automatically communicate information about motor unit pumping operation to the sensing system controller which is further provided to the healthcare professional for life cycle tracking.

The motor unit may include an electrical motor rotating a driver in rolling contact with a surface of the plunger along the axis to move the plunger with rotation of the driver. The driver may be a pinion gear engaging with an axially extending gear rack on the syringe plunger to move the syringe plunger along the axis.

It is thus a feature of at least one embodiment of the present invention to provide direct drive of the plunger and piston reducing the impact of mechanical flexure of the plunger.

A release lever may be moveable to engage the motor with the syringe plunger in a first position and disengage the motor with the syringe plunger in a second position.

It is thus a feature of at least one embodiment of the present invention to allow the plunger to be freely movable so that air may be removed from the tubing.

The plunger may include a set of electronically readable gradations measured by the sensor as the gradations pass by the sensor.

It is thus a feature of at least one embodiment of the present invention to provide direct sensing of plunger shaft movement.

At least one of the plunger and elastomeric piston may include at least one marker detectable by the sensor to determine a relative position between the sensor and the marker wherein the at least one marker is in the piston and the sensor provides a set of sensing elements extending along the axis adjacent to a path of the piston. Longitudinal arms may extend from the housing and flank the tubular barrel to support the set of sensing elements. The sensor may be at least one capacitive sensor.

It is thus a feature of at least one embodiment of the present invention to provide direct sensing of elastomeric piston movement along the tubular barrel.

The tubular barrel may be attached to the housing by a releasable twist lock.

It is thus a feature of at least one embodiment of the present invention to allow the sensing system to be used with a variety of different preloaded syringe tubes and elastomeric pistons.

In an alternative embodiment, the present invention provides a syringe for delivery of a liquid medicament, the syringe including a tubular barrel extending along an axis from an open end to a needle adapter, the open end having outwardly extending grip flanges; a plunger having a first end fitting within the tubular barrel to move the axis within the tubular barrel; a first connector attached to first end of the plunger; an elastomeric piston sealingly fitting within the tubular barrel and movable along the axis within the tubular barrel; a second connector attached to the elastomeric piston and connectable to the first connector to resist separation of the first connector and second connector along the axis.

It is thus a feature of at least one embodiment of the invention to provide a compact preloaded syringe that is later attached to a plunger extending therefrom for convenience in storage and shipping. It is a feature of at least one embodiment of the invention to allow preloaded syringes to be attached to reusable plungers associated with instrumented or motorized delivery systems.

The second connector may be connectable to the first connector with a relative rotation of the first connector with respect to the second connector about the axis.

It is thus a feature of at least one embodiment of the present invention to prevent inadvertent discharge of fluids from the syringe barrel by minimizing pressure on the plunger as it is being attached to the piston.

The first and second connector may provide a predetermined axial separation between the first end of the plunger and a face of the elastomeric piston.

It is thus a feature of at least one embodiment of the present invention to allow the plunger sensor to know absolute position of the plunger by knowing the exact position of the piston.

A shaft collar may support linear translation of the plunger through the collar along the axis and may support outwardly extending finger grips.

It is thus a feature of at least one embodiment of the present invention to allow for manual discharge of fluids from the barrel.

The shaft collar may further support a guide extending perpendicular to the axis providing opposed walls with inwardly facing channels removably receiving the grip flanges of the tubular barrel.

It is thus a feature of at least one embodiment of the present invention to resist pressure on the tubular barrel when fluid is being dispelled from movement of the plunger along the axis.

The grip flanges of the barrel may be secured into the shaft collar by twisting the barrel in the first direction thereby rotating the grip flanges to fit between the channels.

It is thus a feature of at least one embodiment of the present invention to secure the grip flanges beneath the channels using a quarter turn twist lock.

A holder may extend perpendicular to the axis providing opposed walls removably receiving the shaft collar.

It is thus a feature of at least one embodiment of the present invention to allow the preattached tubular barrel and plunger to be installed into the pump housing using a simple drop-down.

A housing may support the holder on a pivotable cover, pivotable to a base supporting a motor unit attached to and stationary with respect to the housing and engaging the plunger to move the plunger with motion of the motor.

It is thus a feature of at least one embodiment of the present invention to automatically engage the plunger to the motor when the cover is locked onto the base.

A housing may support the holder on a pivotable cover, pivotable to a base supporting an electronic sensor attached to and stationary with respect to the base and sensing a sensor element of the syringe to provide direct measurement of motion of the plunger along the axis with respect to the housing to provide an electronic signal indicating movement of the plunger.

It is thus a feature of at least one embodiment of the present invention to automatically align the plunger to the sensor when the pivotable cover is locked onto the base.

A latch may compress the cover against the base to align the plunger with the base.

It is thus a feature of at least one embodiment of the present invention that closure of the cover helps to align and engage the plunger with the motor.

The elastomeric piston may be free from hollow areas that compress during use. The elastomeric piston may be attached to the plunger at respective attachment ends and at least one of the elastomeric piston and the plunger fills a space within the other of the elastomeric piston and the plunger at the attachment ends. The space may be filled with a plastic material.

It is thus a feature of at least one embodiment of the present invention to prevent the deformation of the elastomeric piston when high pressure is applied to the piston during fluid delivery.

An electronic sensor may be attached to at least one of the front and rear wall of the holder and sensing a pressure applied to the front and rear wall to provide an indication of increased pressure along the axis with respect to the housing to provide an electronic signal indicating an occlusion in the syringe.

It is thus a feature of at least one embodiment of the present invention to detect occlusions in the delivery tube using sensors placed in close proximity to the control system of the pump reducing the need for extended wiring.

The second connector may be connectable to the first connector having a female receptor having an inwardly extending tooth engaging with an outwardly extending groove of a male connector.

It is thus a feature of at least one embodiment of the present invention to pre-tension the connection so there is no looseness.

In an alternative embodiment, the present invention provides a syringe for delivery of a liquid medicament, the syringe including a tubular barrel extending along an axis from an open end to a needle adapter, the open end having outwardly extending grip flanges; a plunger having a first end fitting within the tubular barrel to move along the axis within the tubular barrel; a first connector attached to first end of the plunger; an elastomeric piston sealingly fitting within the tubular barrel and movable along the axis within the tubular barrel; a second connector attached to the elastomeric piston and connectable to the first connector to resist separation of the first connector and second connector along the axis wherein the elastomeric piston is free from hollow areas that compress during use.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

BRIEF DESCRIPTION OF THE FIGURES

FIG. 10 is a plot of pressure versus time from the signal obtained from the pressure sensor showing the detection of patient pulse signals used for patient connection verification;

FIG. 11 is a program executable by the control board of FIG. 2 for monitoring the pressure sensor;

FIG. 12 is a view of a plunger piston and interengaging plunger shaft, the latter holding ultrasonic sensor for monitoring volume directly;

DETAILED DESCRIPTION OF THE PREFERRED EMBODIMENT

First Embodiment

Figure 1:
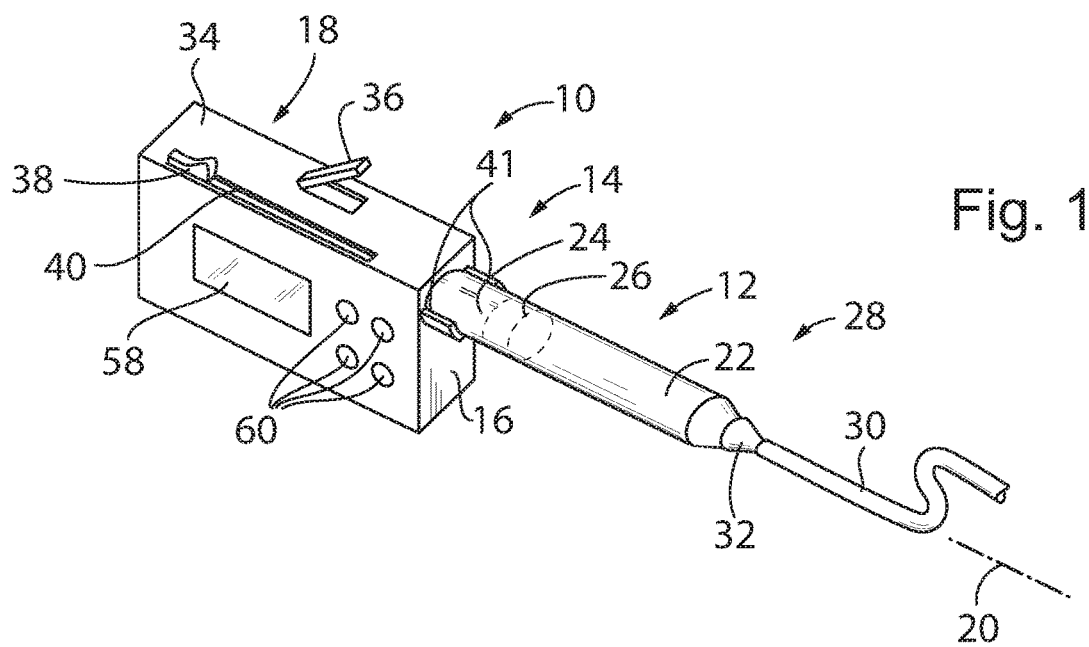
FIG. 1 is a perspective view of a syringe pump according to one embodiment of the present invention providing a compact form factor suitable for portable use and having a housing attached at one end of a syringe, the syringe having a syringe body, a plunger piston, and a plunger shaft.

Referring now to FIG. 1, a syringe pump 10 of the present invention may employ a syringe unit 12 having a proximal end 14 attached to side wall 16 of a pump body 18 so that the syringe unit 12 extends generally along an axis 20.

The syringe unit 12 may be similar to a typical hypodermic syringe and having a syringe tube 22 open at the proximal end 14 to receive a plunger shaft 24 (partially visible in FIG. 1 through the syringe tube 22), the plunger shaft 24 extending away from the proximal end 14 into the pump body 18. The syringe tube 22 may be made of an injection molded inert, non-reactive syringe polymer such as polypropylene and the plunger shaft 24 may be made of an injection molded inert, non-reactive syringe polymer such as polyethylene. The end of the of the plunger shaft 24 within the syringe tube 22 is connected to a plunger piston 26, the latter, for example, being an elastomeric material such as rubber (partially visible through the syringe tube 22 in FIG. 1) or a polymer, and fitting snugly within the volume of the syringe tube 22. The syringe tube 22 may have an outer diameter between 10 mm and 30 mm and may hold a volume typically between 10 mL and 70 mL.

A distal end 28 of the syringe tube 22, opposite the proximal end 14, connects to a tubing 30, for example, by a Luer connector 32 or the like, to provide a continuous passageway between a volume described by an interior of the syringe tube 22 on the distal side of the plunger piston 26 and the tubing.

The pump body 18 may extend away from the syringe unit 12 along axis 20 by a distance approximately equal to the length of the plunger shaft 24 so that the plunger shaft 24 may be fully contained within the pump body 18 when the plunger piston 26 is in its fully retracted position with the syringe unit 12 holding its maximum amount of medicament. An upper wall 34 of the pump body 18 may provide for a release lever 36 that may be raised to partially disengage the internal mechanism of the pump 10 (to be described below) from the plunger shaft 24 reducing resistance on movement of the plunger shaft 24. This movement is possible through the use of slide button 38, also exposed on the upper wall 34 of the pump body 18, engaging internally with the plunger shaft 24. The slide button 38 may be moved manually along an axial slot 40 to manually adjust the position of the plunger shaft 24 within the syringe unit 12.

Figure 2:
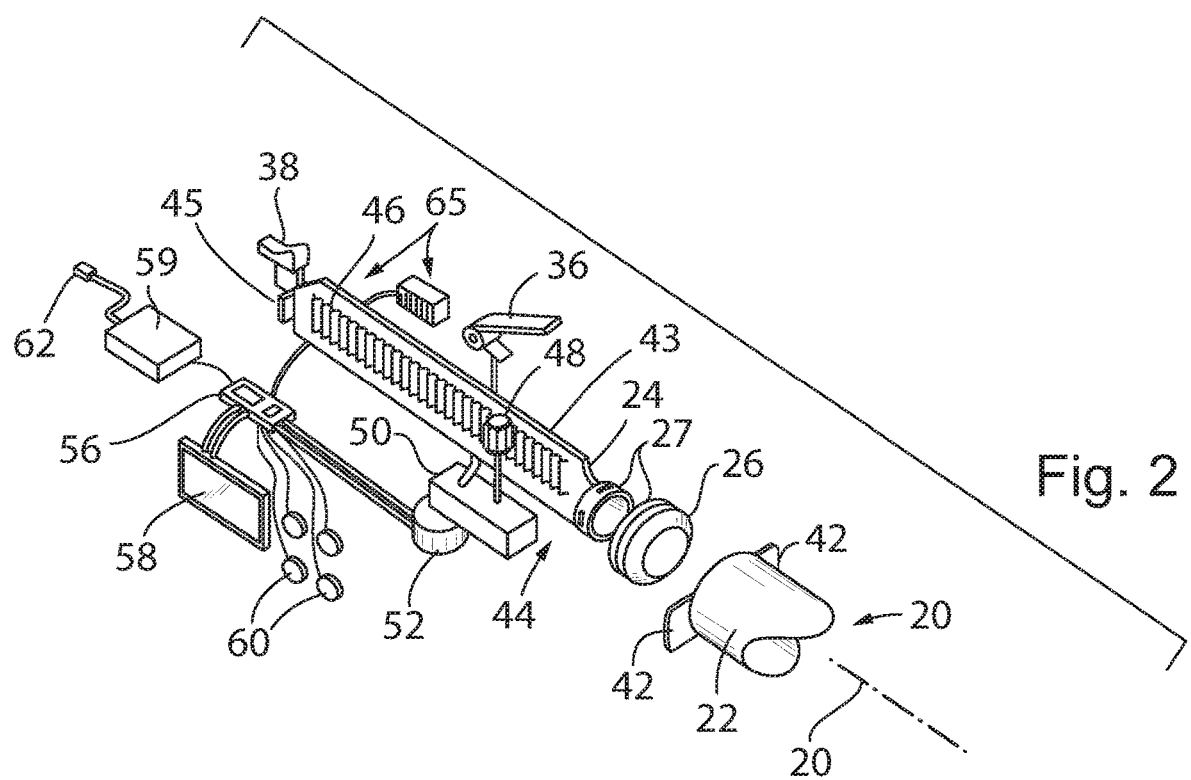
FIG. 2 is an exploded view of internal components of the syringe pump of FIG. 1 showing the detachable plunger piston and plunger shaft and a rack formed directly on the plunger shaft for direct drive by a stepper motor system.

Referring now also to FIG. 2, the pump body 18 may attach to the proximal end of the syringe unit 12 by means of a twist-lock collar 41 receiving laterally and oppositely extending collar ears 42 on the proximal end of the syringe tube 22. The twist-lock collar 41 receives these ears 42 when the syringe tube 22 is given a quarter turn about axis 20. The twist-lock collar 41 may provide for wedge surfaces that engage the ears 42 and compress them with rotation of the syringe tube 22 to provide a releasable yet secure connection.

A similar twist lock 27 may attach the plunger shaft 24 to the plunger piston 26 allowing it to be releasably connected to the plunger piston 26 when the plunger piston 26 is in the syringe tube 22. In this way the plunger shaft 24 may be integrated into the pump body 18 to work with a variety of different preloaded syringe tubes 22 and plunger pistons 26. This twist lock (or bayonet lock) between the plunger piston 26 and the plunger shaft 24 further improves safety in transporting the syringe unit 12 by eliminating the possibility that the plunger shaft 24 may be inadvertently compressed to discharge fluid from the syringe tube 22.

The syringe plunger shaft 24 may provide a more robust structure than provided by a typical syringe shaft, the latter of which must be disposable. For example, the syringe plunger shaft 24 may include a glass-filled thermoplastic material for improved rigidity and resistance to creep or a metallic material.

In one embodiment, the syringe plunger shaft 24 provides an axially and vertically extending beam 43 having a front face 44 holding a gear rack 46 extending generally along axis 20. A rear end of the beam 43 removed from the syringe unit 12 attaches to the slide button 38 discussed above with respect to FIG. 1 and is limited in rearward extent by a stop 45 that may serve as a reference point for calibrating the position of the plunger shaft 24.

A pinion gear 48 supported by a clutching gear train 50 may engage the gear rack 46 so that the gear rack 46 is moved with rotation of the pinion gear 48 moving the syringe plunger shaft 24 controllably along axis 20. The lever 36, discussed above with respect to FIG. 1, may communicate with the clutching gear train 50 to disengage an internal clutch allowing the pinion gear 48 to rotate freely (permitting easy movement of the plunger shaft 24 manually as described above) or to engage that clutch allowing the pinion gear 48 to connect through the clutching gear train 50 (acting as a gear reducer) to a stepper motor 52. In this way, in a first mode with the lever 36 upward, the plunger shaft 24 may be freely movable, for example, to remove air from the tubing 30 of an IV line and, in a second mode, with the lever 36 downward, the plunger shaft 24 may be engaged with the stepper motor 52 for automatic control.

The stepper motor 52 may communicate with the controller microcontroller 56, for example, containing a microcontroller and memory holding programming as will be discussed below. The controller microcontroller 56 may also communicate with a display screen 58 to provide information on the display screen 58, the latter exposed on a front surface of the pump body 18. The controller microcontroller 56 may also communicate with various input buttons 60 allowing control parameters, for example, dose, flow rate, timing, and the like to be input by the user according to techniques well known in the art.

The controller microcontroller 56 may also communicate with a powerpack 59 comprising rechargeable batteries and a charging circuit communicating with a USB jack 62 for external charging through a rear face of the pump body 18 of FIG. 1.

Figure 3:
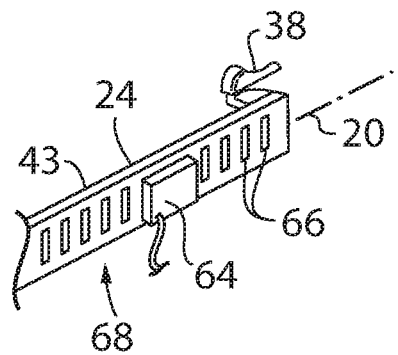
FIG. 3 is a view of an opposite side of the plunger shaft from that depicted in FIG. 2 showing a conductor pattern for direct position sensing of the plunger shaft.
Figure 5:
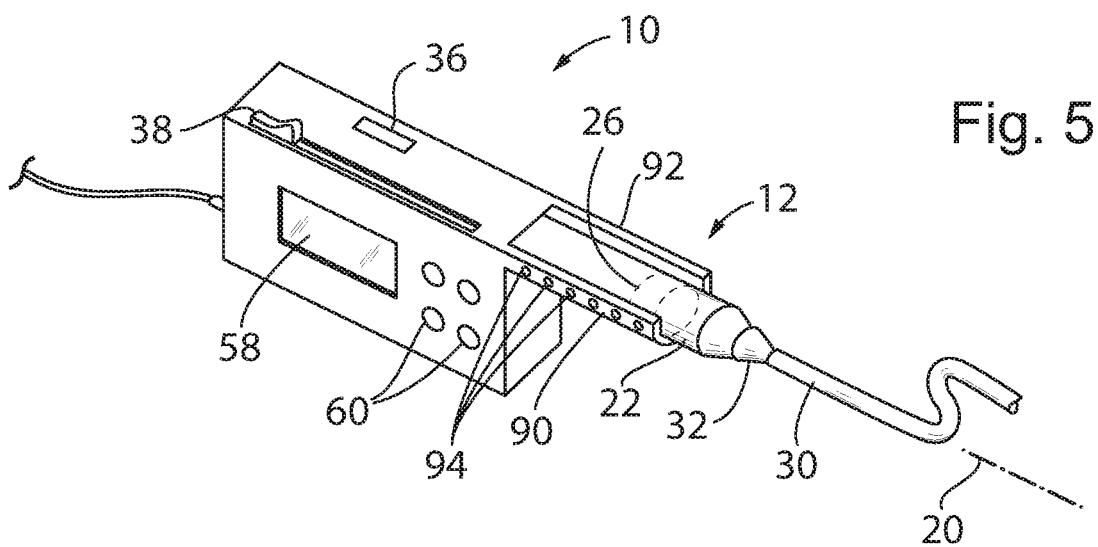
FIG. 5 is a figure similar to FIG. 1 showing an alternative embodiment making direct measurement of the plunger piston.

Referring now to FIG. 3, the controller microcontroller 56 may also communicate with a displacement sensing system 65, for example, providing a single stationary sensor sensing multiple sensor elements such as pattern markings of the moveable syringe plunger shaft 24, or, turning briefly to FIG. 5, multiple stationary sensors sensing a single sensor element of the moveable syringe plunger shaft 24 such as a metal conductor ring or the plunger piston 26.

In one embodiment, a capacitive sensor 64 is stationary with respect to the pump body 18 and reading displacement of a movable capacitive plate pattern 66 attached to the rear side 68 of the beam 43 to provide for precise measurement of movement of the beam 43 along axis 20. This sensing system 65 may make use of circuitry similar to that used by highly precise digital calipers, for example, as described in U.S. Pat. Nos. 4,586,260 and 9,714,846 hereby incorporated by reference.

The invention contemplates that other similar sensing systems may also be used including a linear variable displacement transformer, potentiometer, resolver type optical systems, and other well-known linear transducers having comparable precision.

By directly measuring motion of the plunger shaft 24, mechanical tolerance stack up in the rack 46, pinion gear 48, gear train 50, and stepper motor 52 may be substantially eliminated through a feedback system discussed below. In addition, use of a direct drive on the rack 46 attached to the plunger shaft 24 reduces the impact of mechanical flexure of the plunger shaft 24 as would occur if the force were applied only to its distal end removed from the syringe unit 12 particularly when using a standard syringe constructed of more compliant material. Direct sensing can be understood to provide sensing of the motion of the plunger shaft 24 as part of the sensing system and independent of mechanisms for moving the plunger shaft 24 or measurement of those mechanisms themselves.

Figure 4:
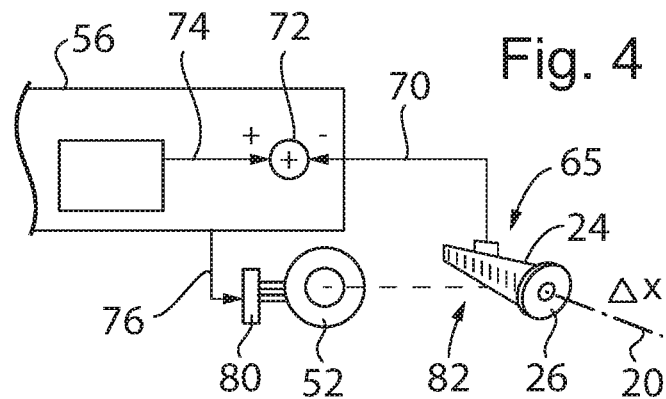
FIG. 4 is a block diagram of the closed loop plunger control implemented by the present invention.

Referring now to FIG. 4, the sensing system 65 may provide for a displacement signal 70 received at a summing junction 72 implemented through software in a memory executed by a processor of the control microcontroller 56. The summing junction 72 also receives a command signal 74, for example, provided by input from the user and describing a desired dose rate, dose volume, or timing. And output from the summing junction 72 provides an error signal 76 to a stepper motor controller 80 driving the stepper motor 52 to move the plunger shaft 24 directly eliminating flexure and tolerance in the mechanical elements between the stepper motor 52 and the rack 46. This error signal provides feedback that eliminates the need for precise monitoring of the operation of the motor and gear train 50.

Referring now to FIG. 5, in an alternative embodiment, a sensing of a position of the plunger piston 26 may be done directly further improving the precision and eliminating tolerance stack up. Such sensing can be done by means of opposed arms 90 and 92 extending generally parallel to axis 20 on flanking sides of the syringe tube 22 of the syringe unit 12. These arms 90 and 92 may hold, respectively, a charge-coupled device photodetector array having multiple elements 94 spaced along axis 20 and a corresponding illuminating LED array directing light through the syringe unit 12. In this way the arms 90 and 92 can detect the position of the plunger piston 26 correctly through the clear or translucent walls of the of the syringe tube 22.

Alternatively, a set of spaced capacitor plates opposed across the syringe tube 22 in arms 90 and 92 may measure a coupling moderated through a metal conductor ring embedded in the plunger piston 26. The plunger piston 26 thus reduces the separation between a capacitor formed by a set of plates in each of arms 90 and 92. In this case the syringe tube 22 is desirably a thermoplastic material having no electrical conductivity.

The control microcontroller 56 may also communicate with one or more ports allowing the exchange of data with the syringe pump 10, for example, for programming the syringe pump 10, receiving maintenance data about the syringe pump 10 and its components, receiving compliance data with respect to drug delivery by the syringe pump 10 and the like, the ports including but not limited to USB, Wi-Fi, NFC or the like and allowing the syringe pump 10 to communicate with a centralized pump station or server or other pumps or devices.

Second Embodiment

Figure 6:
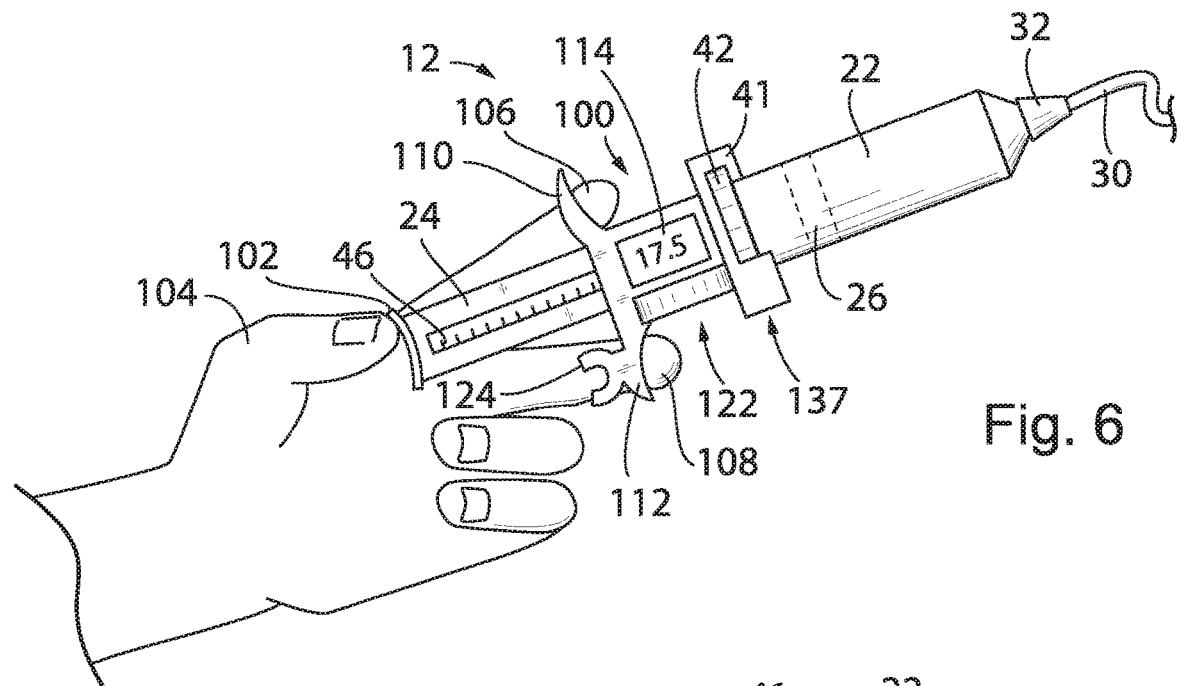
FIG. 6 is a perspective view of an alternative embodiment of the present invention wherein a syringe holder including the syringe plunger and an internal drive and sensing system may be removed from the pump motor for manual use.
Figure 7:
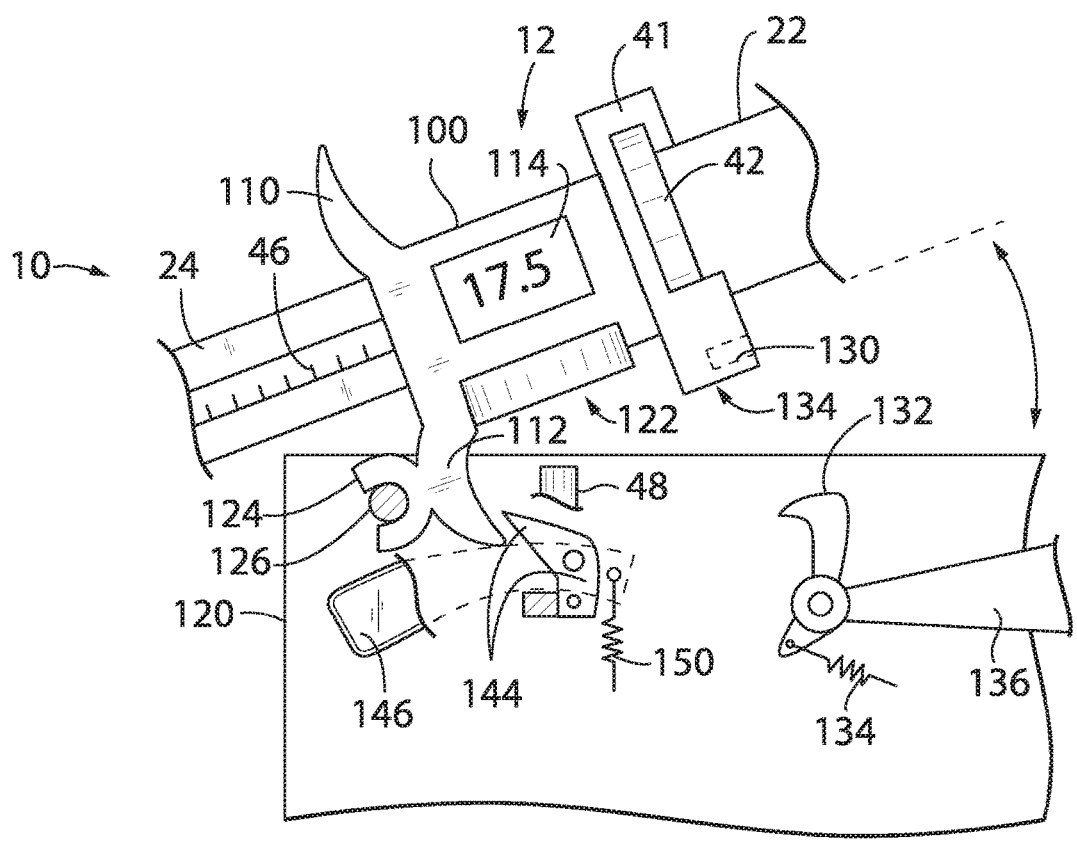
FIG. 7 is a fragmentary view of FIG. 6 showing a pump unit in phantom having a locking mechanism for locking the syringe of FIG. 5 onto a pump motor for automatic operation.

Referring now to FIGS. 6 and 7, a second embodiment of the pump 10 using the functional elements of the first embodiment except as noted may provide for a detachable syringe unit 12 having a self-contained syringe holder 100. The syringe holder 100 incorporates on its front side a twist-lock collar 41 that may receive a syringe tube 22 as discussed above in the first embodiment. As before, the syringe tube 22 may provide a Luer connection 32 attaching to an IV line 30.

The syringe holder 100 may slidably receive therethrough the plunger shaft 24 and may provide a rack 46 or similar engagement mechanism to allow an internal pinion gear 48 (not shown but per the first embodiment) to move the plunger shaft 24 under the influence of a detachable motor unit as will be discussed below.

The distal end of the plunger shaft 24 may provide for a thumb button 102 for manual operation by a healthcare professional who may press on the thumb button 102 with a thumb 104 while having the index and middle finger 106 and 108 respectively stabilized by outwardly extending grip flanges 110 and 112 respectively extending upwardly and downwardly respectively from a rear face of the syringe holder 100. In this way, the healthcare professional, through manual pressure by the thumb 104, may manually operate the plunger shaft 24 without the need for the detachable motor unit (to be discussed below) to move the contained plunger piston 26 through the syringe tube 22.

During this movement of the plunger piston 26, motion of the plunger shaft 24 may be monitored, for example, using a capacitive sensor discussed above with respect to FIG. 3 or alternative sensors also discussed above including optical sensing, magnetic sensing, and the like known for linear displacement measurements. An internal control circuit including a microcontroller and battery and the like may communicate with an LCD display 114 to display the amount of displacement of the piston 26 in volume units. By selection by the user, for example, by controls on the reverse side of the display 114, the display 114 may be zeroed at the time air is removed from the syringe tube 22 in preparation for use. From that point, the display 114 may display the amount of medicament discharged from the syringe tube 22. Alternatively the display 114 may indicate the contained volume prior to pumping and may count downward as material is discharged. In this respect, the display 114 quickly displays an amount of medicament delivered without having to calculate the change in volume manually from gradation printed on the syringe tube 22. High accuracy is obtained because motion of the plunger shaft 24 is measured directly as discussed above with respect to the first embodiment.

Referring now to FIGS. 6 and 7, the syringe unit 12 of FIG. 6 may be optionally and removably attached to a motor unit 120 which includes an electrical motor 52 (not shown but similar to that of the first embodiment) and the gear train discussed above with respect to FIG. 2 terminating in pinion gear 48. This spur gear 48 may communicate with a ring gear (not shown) contained in gear shroud 122 attached to a lower face of the syringe holder 100 when the syringe unit 12 is mounted on the motor unit 120 as will be discussed. When the syringe unit 12 is removed from the motor unit 120, the syringe may be operated manually by pressing on the thumb button 102 of the shaft 24 as described above, or by turning a knob 101 communicating either directly or through a reducing gear train with a gear driving the rack 46 also driven by gear 48 for fine control of the pumping volume.

Thus, when the syringe is used manually, the movement of the piston can be coarsely controlled by hand pushing the end of the plunger, or finely controlled by turning a knob, which drives the plunger to move slowly. The displacement of the piston (therefore the volume change) can be continuously monitored. In one embodiment, the volume change information can be read on the built-in display screen; wirelessly transmitted to the pump; or directly to a remote server.

Figure 8:
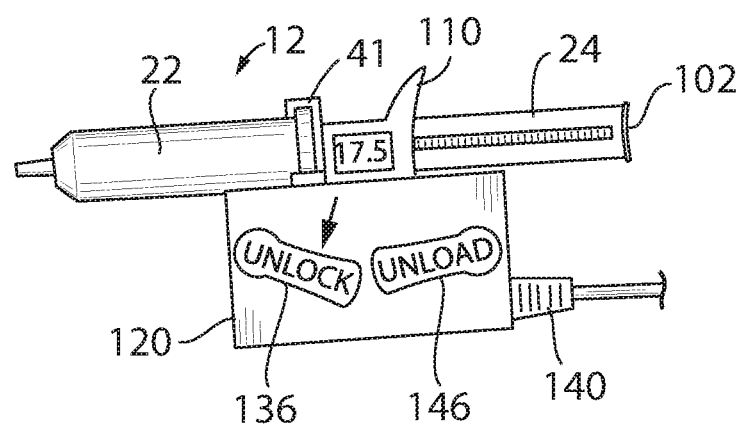
FIG. 8 is a rear side view of the pump unit of FIG. 7 showing the unlock and unload levers used for the attachment process.

In this regard, a rear surface of the lower grip flange 112 may provide for a rear-opening fork 124 receiving a horizontally extending pin 126 within a housing of the motor unit 120. Pivoting about pin 126, a lower portion of the twist-lock collar 41 may swing downwardly through an upwardly open portion of the housing of the motor unit 120 where a notch 130 in the lower end of the twist lock collar 41 may be received and retained by a spring-loaded catch 132. As so positioned, the syringe tube 22 is generally parallel to the top surface of the generally rectangular housing of the motor unit 120. In this engaged position, the syringe unit 12 is locked to the motor unit 120 through the combined effect of pin 126 engaging fork 124 and catch 132 which is spring-loaded by spring 134 engaging notch 130. Catch 132 includes an externally accessible unlock lever 136 manually operable by the user when it is desired to release the syringe unit 12 as shown in FIG. 8.

When the syringe unit 12 is locked to the motor unit 120, spur gear 48 may drive (through an intervening gear train within the syringe holder 100) the plunger shaft 24 as discussed above with respect to the first embodiment. Electrical connectors 137 at the bottom of the twist-lock collar 41 engage corresponding connectors in the motor unit 120 so that an internal microcontroller 56 may control the syringe unit 12 as discussed above in the first embodiment providing motor activation signals and receiving sensor signals indicating the amount of drug dispensed. The syringe holder 100 may communicate its cumulative operating time to the motor unit 120 and the motor unit 120 may also track its operating time to disable operation at a predetermined lifespan reducing the chance of failure when such lifespan is exceeded. This lifespan and a warning may be displayed to the user either through the display 114 or similar display on the motor unit 120.

Thus, in the case of a portable syringe holder with sensor(s) integrated, the life of the disposable of the syringe holder can be monitored by the pump. The syringe holder itself can be checked by the user and a display (or LED indicator) can provide the user with information that the syringe holder is ready to be used, or its life has been reached.

The motor unit 120 may have a self-contained power source such as a battery or may receive electrical power over an electrical/data USB connector 140 which may be used to power the motor unit 120 and to receive output data about the pumping operation.

In this regard, the controller 56 within the syringe unit 12 may store within a memory and further communicate information, for example wirelessly through a transmitter, about how much material has been pumped and data from other sensors such as near field sensors that can operate to read tags on the syringe tube 22 (to be discussed below) to read the type of medicine being delivered and its volume and other data such as the identification of the patient receiving the drug and the like which may be used to provide information to the healthcare professional as well as monitor drug custody from the pharmacist throughout the entire delivery cycle including delivery to the patient and ultimate secure disposal of any remaining material.

After the syringe unit 12 is installed in the motor unit 120, activation of the unlock lever 136 allows the syringe unit 12 to be pivoted upward about pivot pin 126 away from the motor unit 120 as depicted in FIG. 7, and a secondary catch 144 attached to an unload lever 146 prevents further upward tipping and complete disengagement from the pin 126. This partial upward pivoted position allows the syringe unit 12 to be removed and replaced without separation of the syringe holder 100 from the motor unit 120. Pressing downward on the unload lever 146 (clockwise as shown in FIG. 8) allows further upward pivoting of the syringe unit 12 so that it may be fully disengaged from the motor unit 120. During installation of the syringe unit 12, the catch 144 is naturally rotated in a counterclockwise position as shown in FIG. 7 until the syringe unit 12 is fully engaged with the motor unit 120 upon which the catch 144 slips past the end of the flange 112 under the influence of a spring 150 so as to provide the partial pivoting just discussed.

Referring again to FIG. 8, it will be understood that when the syringe unit 12 is engaged with the pump motor unit 120 and the plunger shaft 24 is driven by the pump motor unit 12, there is a locking mechanism to lock the syringe tube 22 in place in the syringe unit 12. This locking mechanism may be interference between upper portions 121 of the housing of the pump motor unit 120 flanking the tabs of the collar 41 of the syringe tube 22 which prevent rotational movement of the syringe tube 22 and upwardly extending fingers 123 which flank the sides of plunger shaft 24 preventing its rotation. Engagement of the gear 48 (shown in FIG. 7) with the internal mechanism of the syringe unit 12 resists manual movement of the plunger shaft 24 along its axis. The motor 52 may also automatically lock the plunger shaft 24 from manual movement when the necessary volume (i.e., dose volume) of medicine has been pumped to prevent over-delivery of medicament.

When the syringe unit 12 is released from the motor unit 120, the syringe tube 22 can be rotated (together with the removable plunger shaft 24) for syringe replacement.

As noted above, unlock lever 136 (shown in FIG. 7) locks the syringe unit 12 on the pump motor unit 120. When released, the syringe unit 12 can be removed from the pump motor unit 120 and once the syringe unit 12 is so removed manual operation of the syringe is enabled.

The separability of the syringe unit 12 from the motor unit 120 allows the healthcare professional to provide manual administration of drugs for a certain period of time and then to invoke the automatic operation provided by the motor unit 120. Generally, the motor unit 120 may have a display screen 58 and control button 60 otherwise operate in the manner discussed with respect to the first embodiment to provide automatic pumping capabilities.

Figure 9:
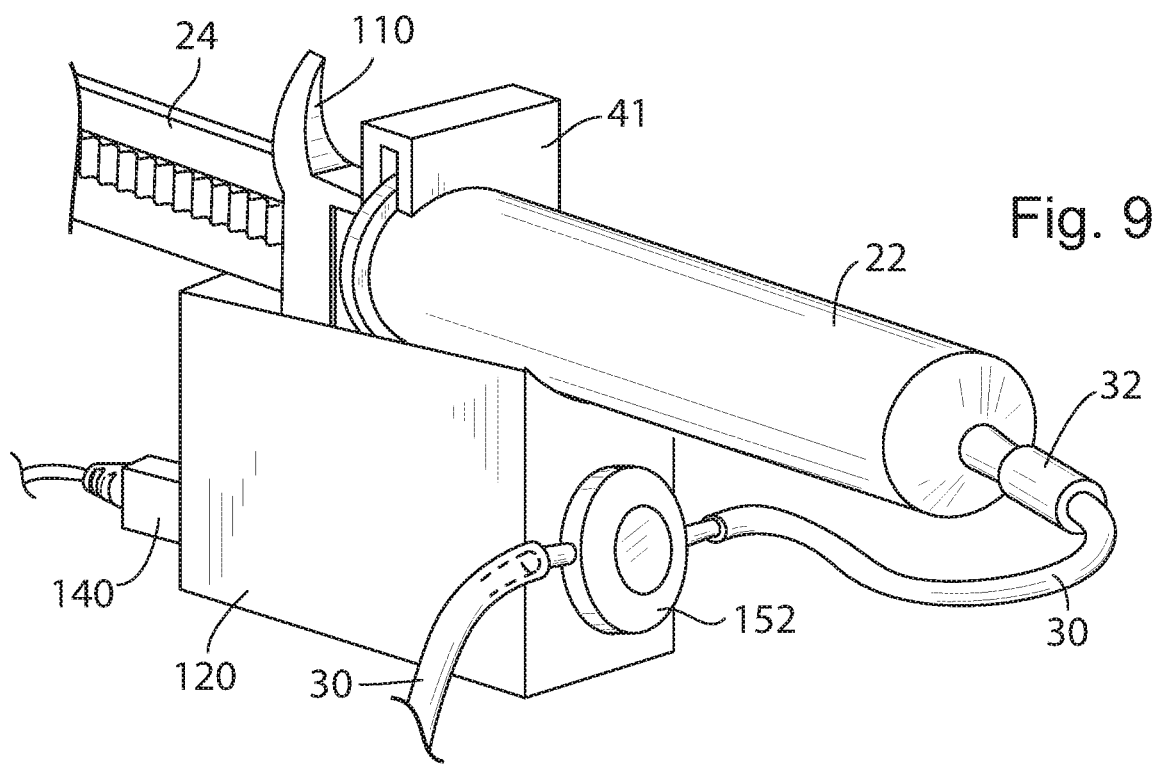
FIG. 9 is a perspective view of the syringe attached to the pump unit showing a pressure sensor that may accept a docking diaphragm being part of an IV kit.

Referring now to FIG. 9, a disposable IV kit may include the Luer 32 and tubing 30 with a spliced-in diaphragm element 152 which may attach through snaps or the like to the front of the housing of the motor unit 120. As so attached, a thin diaphragm (not shown) at the rear of the diaphragm element 152 engages a sensitive pressure sensor for the measurement of internal pressure of the IV line tubing 30 while isolating liquid in the IV line 30 from contact with the pressure sensor.

Referring now to FIG. 10 the pressure sensor may provide a pressure signal 154 that may be used to detect occlusion of the IV line tubing 30 if pressure rises to an occlusion level 156 and then detect pump failure if pressure does not rise above a pump active level 158. The pressure signal 154 may be further processed, for example, by a bandpass filtering system implemented algorithmically by the controller 56 of the motor unit 120 to extract a patient heartbeat signal 160 that may be used to confirm that the IV line tubing 30 is in fact connected to the patient and to provide an alarm condition otherwise.

Referring now to FIG. 11, the controller 56 in this regard may receive the pressure signal as indicated by process block 162 and may control the motor 52 (shown in FIG. 2) at a process block 164 to provide the desired pumping schedule while observing the limits 156 and 158 discussed above with respect to FIG. 10. The heartbeat signal 160 extracted as indicated by process block 166 is monitored and if a patient is detected through the patient's detected heartbeat per decision block 168, the program proceeds to decision block 170 to determine if the necessary volume of medicine has been pumped. If at decision block 168 there is no patient heartbeat signal detected, an alarm condition is entered as indicated by process block 172 where the pumping is stopped and a healthcare professional is summoned to make sure that the needle to the patient has not been dislodged.

At decision block 170, if the volume limit has not been reached, the program loops back to process block 162. Otherwise the program causes pumping to stop per convention as indicated by process block 174.

Referring now to FIG. 12, in an additional embodiment, the end of the shaft 24 engaging the piston 26 may provide for an acoustic transducer 180 that can communicate sound (transmitting and receiving) through a thin diaphragm wall 183 of the piston 26 into the liquid drug 182 contained in the syringe tube 22. A natural resonant frequency of the cavity provided in the syringe tube 22 may be processed to provide a spectrum 184 whose peaks may be analyzed to determine the various dimensions of the cavity and hence the actual volume of the cavity for direct measurement of volume pumped. Other techniques of direct measurements of volume may be contemplated including those that look at capacitive sensing and the like to provide a direct measurement of volume as opposed to deducing volume from known dimensions of the syringe tube 22 and linear displacement of the piston 26 for high degrees of accuracy.

Figure 13:
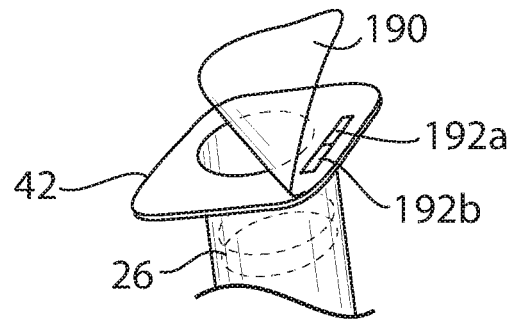
FIG. 13 is a view of a pre-prepared and filled syringe having a contained plunger and a sealed opening for installation in the syringe holder of FIG. 6.

Referring now also to FIG. 13, the ability to disconnect the piston 26 in the syringe tube 22 from a twist lock connector 27 of the plunger shaft 24 allows the syringe tube 22 to be prefilled with medicine, transported, and later attached to the syringe unit 12 using the twist-lock collar 41 shown in FIG. 5. After filling of the syringe tube 22 and installation of the piston 26, an adhesive cover 190 may be adhered to the collar 41 at the open end of the syringe tube 22 to provide leak prevention and security against tampering. The adhesive cover 190 may be such as to be tamper evident when it is opened, for example, by tearing or refusing to re-adhere or the like and may include labels 192 indicating the drug and or patient in both human and machine readable form, for example, using near field RFID technology. In this way the contents of the syringe tube 22, proper patient, and dose information may be communicated electronically to the syringe holder 100 and ultimately to the motor unit 120 and connector 140 as discussed above for use in controlling the drug delivery.

In one embodiment the label 192 may have a portion 192a affixed to the syringe tube 22 and a portion 192b attached to the adhesive cover 190 to be removed when the syringe is put in use. An initial scanning of the assembled label 192 and syringe tube 22 can be performed to confirm the existence of an unused syringe. After the label 192 is removed and discarded, any scanning will reveal that the syringe has been previously used helping to eliminate delivery errors or diversion of drugs. A portion of the label 192a remaining on the syringe tube 22 may be used to validate disposal of the syringe or later drug identification.

Thus, one or more sealing labels can be applied to the syringe with removable syringe plunger shaft to serve as sterility barrier and information carrier. The label can be applied to the opening of the syringe to seal the cylinder and it can carry drug information in the form of a barcode. When removing the sealing label, the portion with barcode can be left on the syringe for drug identification by user, and/or by the pump. The pump can read barcode information from the syringe, or read information from RFID on the syringe, and configure the pump for infusion.

Figure 14:
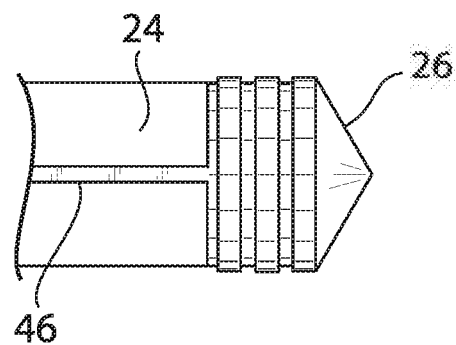
FIG. 14 is a fragmentary end view of the plunger shaft and piston of the syringe typically constructed of different polymer materials.
Figure 15:
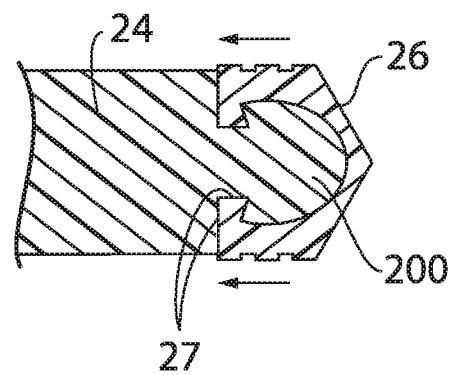
FIG. 15 is a cross-sectional view in elevation of the fragmentary view of FIG. 14 showing a syringe design with preloaded piston elastomer and a gapless support of the rear of the piston by the plunger shaft.

Referring now to FIGS. 14 and 15, the plunger shaft 24 will normally be constructed of a relatively rigid polymer material while the piston 26 is constructed of an elastomer having rubber like qualities. The present invention provides a space filling attachment between the end of the plunger shaft 24 and a rear surface of the piston 26, for example, by using a space filling mushroom portion 200 fully supporting the rear side of the piston 26 to eliminate an initial deformation of the piston 26 when pressure is applied by the plunger shaft 24 such as could be misinterpreted as a discharging of volume from the syringe. In this regard, the twist lock elements 27 may provide a preload stretching of the sidewalls of the piston 26 rearward to remove any gap or initial deformation of the piston 26 when the syringe is used. In an alternative configuration, the mushroom portion 200 may be constructed of a rigid plastic and glued to the piston 26 or attached by other space filling means. The mushroom portion 200 may then provide for a rigid twist lock to the shaft 24 (not shown).

In summary, to improve precision, piston 26 can be optimized to minimize variation during drug delivery. The specific means can be:

A. Remove any space between the piston 26 and the supporting portion of the piston shaft 24. Optionally, the rubber of the piston 26 can be glued to a solid end of the piston shaft 24. Alternatively, the rubber dome of the piston 26 can have a "mushroom shaped" socket (as shown in FIG. 15) to engage tightly with the mushroom portion 200 shown in FIG. 15 if glue is not to be used due to contamination or material compatibility concern. (Traditionally, there is a gap between the rubber dome and the structure of the shaft 24 or the piston is can be compartmented at the tip which leaves some space for the rubber dome of the piston 26 to deform before any fluid can be delivered).

B. preload the rubber layer of the piston 26 so it is under tension once assembled with the attached end of the shaft 24 which will reduce changes in the piston 26 under pressure causing changes in the delivery volume of fluid from to the flexibility of the rubber tip and pressure changes in the line.

Figure 16:
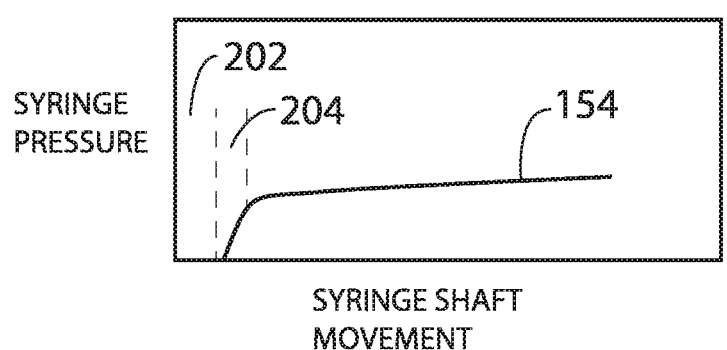
FIG. 16 is a plot of syringe pressure using the sensor of FIG. 11 versus syringe shaft movement monitored using a sensor such as shown in FIG. 3 indicating a "windup" before actual dispensing by the syringe such as can be compensated by the controller.

Referring now to FIG. 16, in addition or alternatively, initial "wind up" where the shaft 24 is moving but there is no net flow of medicine from the syringe because of take-up of mechanical gaps, for example, between the gears 48 and rack 46, initial flexure of the piston 26 (discussed above) or other compliance mechanisms, for example, including expansion of the IV tubing etc. may be detected by monitoring syringe pressure using the pressure sensor discussed above versus syringe shaft movement as detected for example using sensing system 65 discussed above. The signal 154 may be analyzed by the controller 56 in the motor unit 120 to identify a dead band 202 where movement of the shaft 24 doesn't correspond to actual pumping of fluid indicated by lack of pressure and compliance band 204 where there is pumping a fluid but less than would be indicated by movement of the syringe shaft 24 which may be empirically measured, both the dead band 202 and compliance band 204 being used to discount the calculated pumped volume to provide a more precise measurement of pumped volume on the display 114 or 58.

This embodiment provides a way of improving the precision for delivery in that motor current signal can be monitored to determine if the plunger head has been fully engaged and the "real" delivery of fluid started. By taking account the initial motor movement which does not result in true fluid delivery, the calculation in the infusion program can be more accurate. This initial variation is small but compensating it can make the system more accurate.

Figure 17:
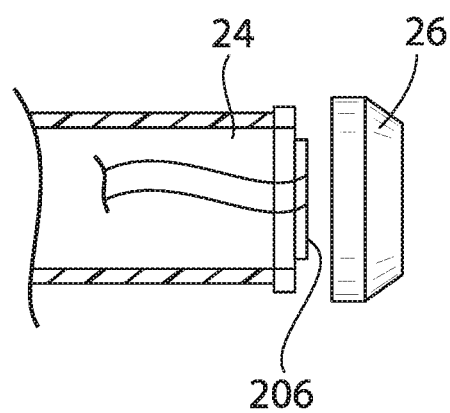
FIG. 17 is a view of a plunger piston and interengaging plunger shaft, the latter holding a pressure sensor for monitoring pressure against the plunger shaft.
Figure 18:
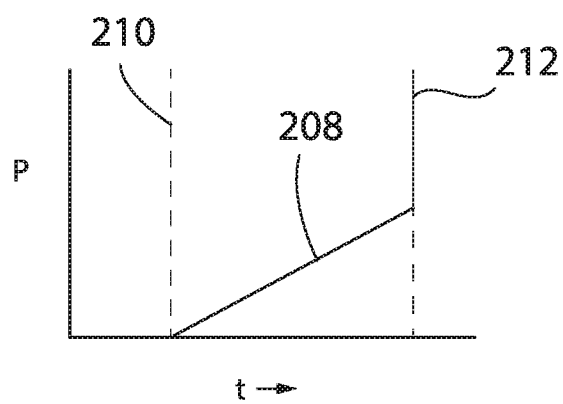
FIG. 18 is a plot of pressure versus time from the signal obtained from the pressure sensor showing the detection of engagement of the plunger piston with the plunger shaft and an occlusion within the IV line.

Referring now to FIGS. 17 and 18, in an additional embodiment, the end of the shaft 24 engaging the piston 26 may provide for a pressure sensor 206 that can wirelessly or through a wired connection communicate a pressure signal 208 to the microcontroller 56 that may be used to detect an engagement of the piston 26 to the shaft 24 at engagement time 210 when the pressure goes from zero (piston 26 and shaft 24 are disengaged) to an increasing function as the shaft 24 is advanced at a constant rate through the syringe tube 22. The pressure sensor 206 can also detect an occlusion of the IV line tubing 30 at occlusion time 212 when pressure increases rapidly (spikes) as the shaft 24 is advanced through the syringe tube 22 causing high pressure build-up. The pressure sensor 206 may be a strain gauge or piezoelectric sensor indicating a pressure against the shaft 24 by the piston 26 and fluid within the syringe tube 22. The pressure sensor 206 can be powered by a battery or by connecting to the power supply of the pump 10. The pressure sensor 206 can be installed inside the piston 26 and just behind a thin rubber layer so fluid pressure can be directly sensed as well.

Third Embodiment

Figure 19:
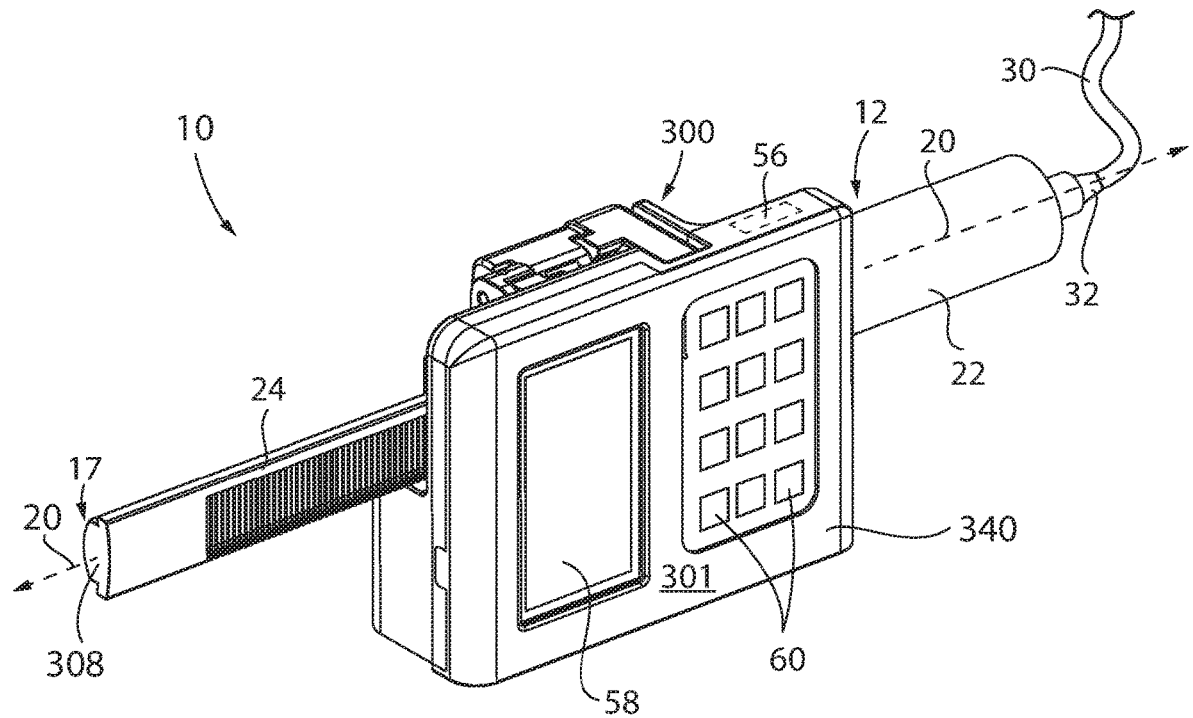
FIG. 19 is a perspective view of an alternative embodiment of the present invention wherein a front side of a syringe holder has a housing releasably receiving a syringe.
Figure 20:
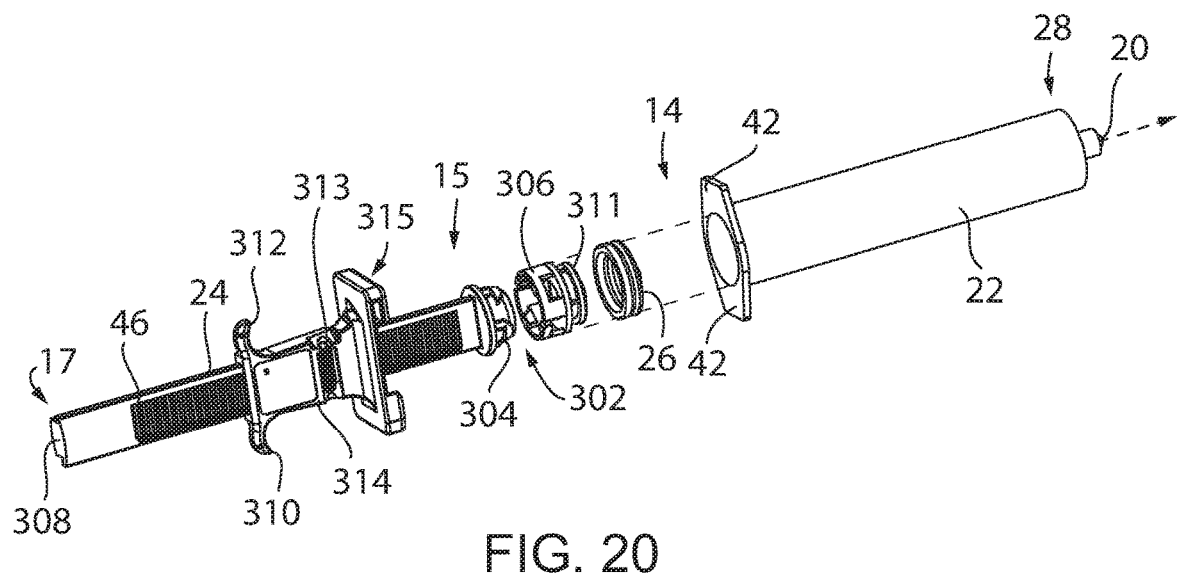
FIG. 20 is an exploded view of the syringe of FIG. 19, the syringe having a syringe tube, a piston, a plunger shaft; and a shaft collar, and showing the syringe tube receiving the detachable plunger piston and plunger shaft, the plunger shaft supported by a collar having grip flanges and received within the housing of FIG. 19.

Referring now to FIGS. 19 and 20, a third embodiment of the pump 10 using the functional elements of the first and second embodiment except as noted may provide for a removable syringe unit 12 removably received within a pump housing 300. The pump housing 300 incorporates on its front side 301, a display screen 58 and various input buttons 60 as discussed above with respect to the first embodiment to provide display information to the user and to communicate various inputs to an internal controller microcontroller 56 allowing for control of the syringe unit 12. The input buttons 60 may be on a keypad or a liquid crystal display screen with virtual buttons such as those found on smart phones and tablets.

The syringe unit 12, attachable to the pump housing 300, includes a syringe tube 22 extending along an axis 20 and open at the proximal end 14 to receive a proximal end 15 of a plunger shaft 24, the plunger shaft 24 extending away from the proximal end 14 of the syringe tube 22 through the pump housing 300 to a distal end 17 providing a thumb button 308 that can be used to press inward on the plunger shaft 24. As before, the syringe tube 22 may provide oppositely extending collar ears 42 extending perpendicular to the axis 20 on the proximal end 14 and a Luer connector 32 attaching it to an IV line 30 on the distal end 28.

Removably received within the syringe tube 22 is a piston 26 being an elastomeric material such as rubber, and as discussed above in the first embodiment. The piston 26 seals against the inner surface of the syringe tube 22 in the manner of a conventional syringe. Referring briefly again to FIG. 15, the piston 26 is substantially free from voids that would compress and thus change the separation between the front of the piston 26 and the plunger shaft 24 and in one embodiment may be constructed with a space filling attachment between the end of the plunger shaft 24 and a rear surface of the piston 26 as discussed above in the second embodiment. For example, a space filling mushroom portion 200, constructed of a rigid plastic, may fully support the rear side of the piston 26 to eliminate an initial deformation of the piston 26 when pressure is applied by the plunger shaft 24. The space filling mushroom portion 200 may be integral with the plunger shaft 24 and extend into the piston 26, as shown in FIG. 15, or alternatively, glued to the piston 26 and extending into the plunger shaft 24 in a similar manner to prevent deformation of the piston 26 when fluid is discharged from the syringe.

Figure 21:
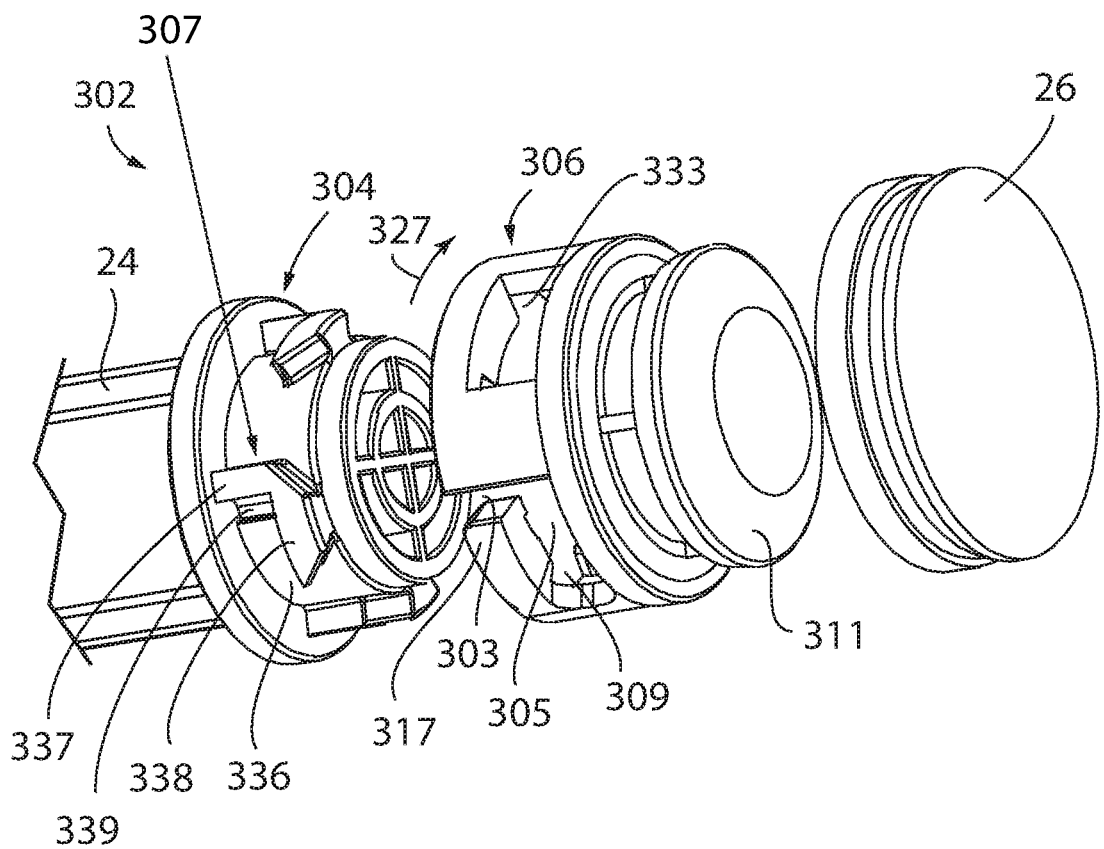
FIG. 21 is an enlarged view of the connectors of the detachable plunger piston and plunger shaft of FIG. 20 having a fastening mechanism with an inwardly extending tooth of the plunger piston engaging with an outwardly extending groove of the plunger shaft.

Referring also to FIG. 21, a twist lock 302 may attach the plunger shaft 24 to the plunger piston 26 allowing the plunger shaft 24 to be releasably connected to the plunger piston 26 when the plunger piston 26 is in the syringe tube 22. The twist lock 302 (or bayonet lock) allows the plunger shaft 24 to be attached to the plunger piston 26 with a simple twisting motion and without compressing the plunger piston 26 into the syringe tube 22 which would undesirably discharge fluid from the syringe tube 22. The twist lock 302 provides a positive stop to rotation that produces a fixed relative location along the axis between the front of the plunger and the front surface of the piston.

The twist lock 302 may comprise a locking connector 304 of the plunger shaft 24 engaging with a locking connector 306 of the plunger piston 26. The locking connector 306 may include a cylindrical inner frame 311 receiving the rear side of the piston 26 on one end and connecting with the plunger shaft 24 on the opposite end. In one embodiment, the locking connector 306 may include the space filling mushroom portion 200 or receive the space filling mushroom portion 200 of the piston 26, as discussed above.

Generally, one of the locking connectors 304, 306 may include a radial pin 307 engaging with the other of the locking connectors 304, 306 having an L-shaped slot 309.

The L-shaped slot 309 receives the pin 307 into a vertical arm 303 of the L-shaped slot 309, the vertical arm 303 extending along the axis 20, and rotates the pin 307 across a horizontal arm 305, the horizontal arm 305 extending radially perpendicular to the axis 20, an end of the horizontal arm 305 stopping the pin 307 from further rotation and from further movement of the locking connectors 304, 306 along the axis 20, keeping the plunger shaft 24 and the plunger piston 26 locked together. In one example, the twist lock 302 may connect the plunger shaft 24 to the plunger piston 26 with a clockwise or counterclockwise approximate quarter turn.

Figure 22:
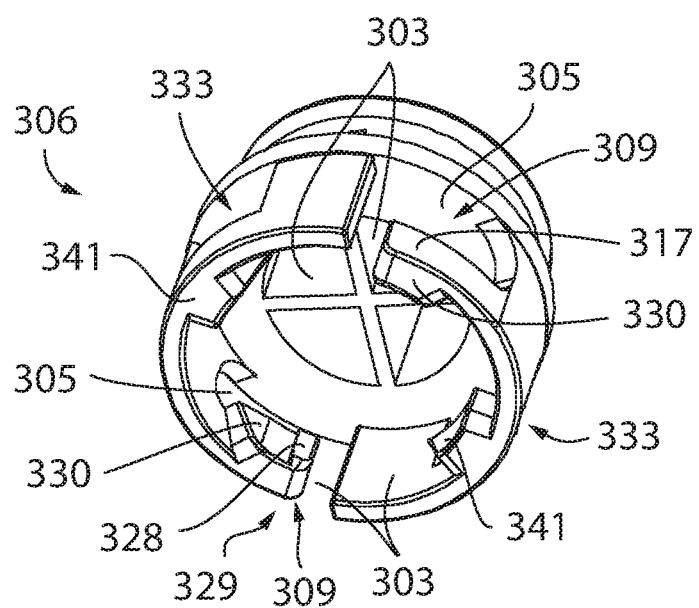
FIG. 22 is an interior view of the plunger piston of FIG. 20 with a female receptor having a flexing arm holding the inwardly extending tooth.

Referring specifically to FIGS. 21 and 22, in one embodiment, the locking connector 306 of the plunger piston 26 may be a cylinder housing including two L-shaped slots 309 (female receptor) allowing the locking connector 306 to receive therein the radial pin 307 (male connector) of the locking connector 304 of the plunger shaft 24. The L-shaped slot 309 of the locking connector 306 may include a vertical arm 303 extending along the axis 20 and further extending to a horizontal arm 305, extending radially perpendicular to the axis 20. The vertical arm 303 and horizontal arm 305 are separated by a cantilevered arm 317 extending radially in a opposite direction as the horizontal arm 305 to separate the horizontal arm 305 from an outer edge of the locking connector 306 and thus partially forming the L-shaped slot 309. An inner surface of the cantilevered arm 317 supports an inwardly extending block 330 supporting an inwardly extending tooth 328 extending inwardly at a distal end 329 of the cantilevered arm 317. As further described below, the cantilevered arm 317 may flex to move the inwardly extending tooth 328 slightly inward and outward. The cylindrical housing of the locking connector 306 of the plunger piston 26 may also include two rectangular openings 333 spaced between the L-shaped slots 309 and having inwardly extending blocks 341 positioned below the rectangular openings 333.

An exterior surface 336 of the locking connector 304 of the plunger shaft 24 may support four evenly spaced pins 307 engaging with the L-shaped slots 309 and rectangular openings 333 of the connector 306. The pins 307 may extend outwardly from an exterior surface 336 of the locking connector 304 and take an L-shape configuration with a vertical arm 337 extending toward the connector 306 along axis 20 and further extending to a horizontal arm 338 extending perpendicular to the axis 20. In this respect, the shape of the pins 307 may correspond with the shape of the L-shaped slots 309, and the horizontal arm 338 may correspond with the shape of the rectangular openings 333. Below the horizontal arm 338 and within the inner bend of the pins 307 may be a rectangular groove 339 shaped to receive the tooth 328 of the cantilevered arm 317 of the locking connector 306 as further discussed below.

The locking connectors 304, 306 of the plunger shaft 24 and plunger piston 26, respectively, may be coupled by inserting the locking connector 304 of the plunger shaft 24 into the interior space of the locking connector 306 of the plunger piston 26 such that the four evenly spaced pins 307 are inserted along the vertical arm 303 of the L-shaped slots 309. The two oppositely positioned L-shaped slots 309, spaced 180 degrees apart, and the two rectangular openings 333, spaced 180 degrees apart, may receive the radial pins 307 of the locking connector 304 along axis 20.

The locking connector 304 is then rotated about direction 327 to allow the horizontal arm 338 of the radial pins 307 to rotate, for example by a quarter turn, either into the horizontal arm 305 of the L-shaped slots 209 or into the rectangular openings 333. The vertical arm 337 of the radial pins 307 is stopped from further rotation by the inwardly extending wedge surface 330 of the L-shaped slot 309 or by the inwardly extending blocks 341 of the rectangular openings 333. The inwardly extending tooth 328 is also locked into the rectangular groove 339. The cantilevered arm 317 may be flexed slightly outward during engagement.

In order to disengage the inwardly extending tooth 328 from the rectangular groove 339, the locking connector 304 is rotated in an opposite direction, opposite of direction 327, to remove the inwardly extending tooth 328 from the rectangular groove 339. The horizontal arm 338 of the radial pins 307 is rotated out from the horizontal arm 305 of the L-shaped slots 209 or from the rectangular openings 333, and the vertical arm 303 of the L-shaped slots 309 are removed along the vertical arm 303 of the L-shaped slots 309. The cantilevered arm 317 may be flexed slightly outward during disengagement. The syringe tube 22 may provide enough clearance to allow for the slight outward flexure of the cantilevered arm 317 during engagement and disengagement.

Figure 27:
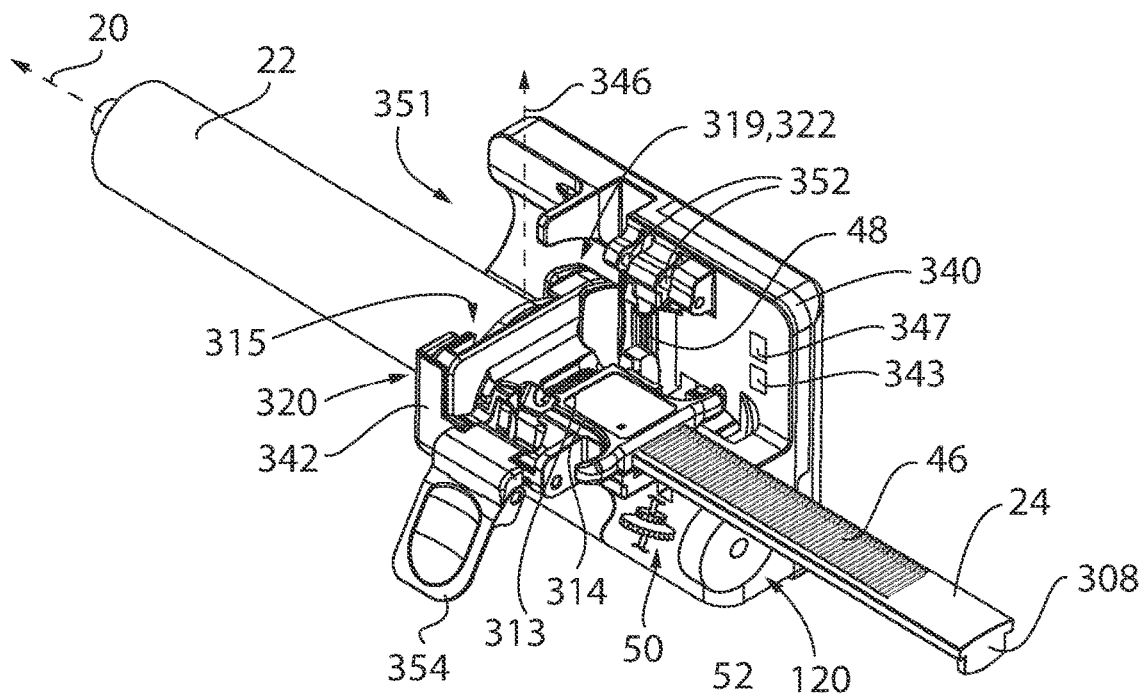
FIG. 27 is a view similar to FIG. 26 where the syringe holder is pivoted to a disengage position with respect to the housing to load and unload the syringe.

Referring again to FIGS. 19 and 20, as previously discussed, the plunger shaft 24 may provide a rack 46 or similar engagement mechanism to allow an internal pinion gear 48, as shown in FIG. 27, to move the plunger shaft 24 under the influence of a motor 52. Alternatively, the plunger shaft 24 may move manually under the influence of the user pressing on the thumb button 308.

A distal end of the plunger shaft 24 may provide a thumb button 308 pressed by the thumb of a healthcare professional while the index and middle finger are stabilized by outwardly extending grip flanges 310, 312 supported by a shaft collar 314 surrounding a proximal end of the plunger shaft 24. The shaft collar 314 may be positioned distal to the locking connector 304 to slidably receive the plunger shaft 24 therethrough. The shaft collar 314 may include a rectangular opening 313 allowing for the rack 46 to be exposed and engaging with the pinion gear 48 as further described below. The shaft collar 314 may also include a guide 315 received by the pump housing 300. The guide 315 may provide a panel extending perpendicular to the plunger shaft 24 and anchoring the grip flanges 310, 312 with respect to movement of the sliding plunger shaft 24 along the axis 20 therethrough, and further receiving the collar ears 42 of the syringe tube 22 as discussed further below Referring to FIGS. 25-27, the pump housing 300 may support thereon a syringe holder 320 that may be pivotably attached to the pump housing 300 to slidably receive therein the guide 315 of the shaft collar 314 and the oppositely extending collar ears 42 of the syringe tube 22 to stabilize the syringe unit 12 within the pump housing 300. Further, when the syringe holder 320 and supported syringe unit 12 are in an engaged position, the syringe holder 320 allows the rack 46 of the syringe holder 320 to engage the internal pinion gear 48 and internal sensing mechanisms to detect, for example, an amount of fluid delivery from the syringe tube 22 and fluid blockages in the delivery tubes as further described below.

Figure 25:
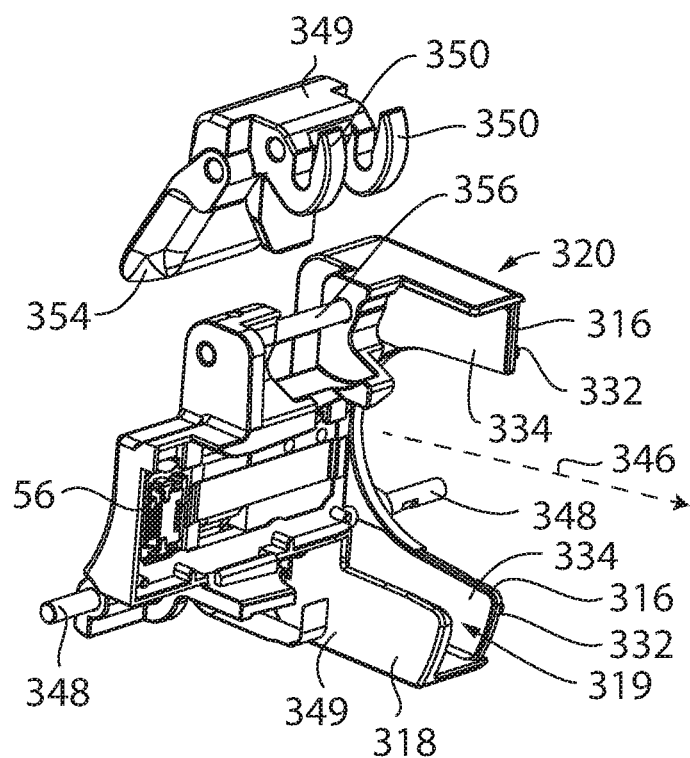
FIG. 25 is a perspective view of the syringe holder configured to receive a collar of the syringe plunger and collar ears of the syringe tube, and having a pressure sensor on its inner walls for monitoring pressure of the collar ears of the syringe tube against the inner walls of the syringe holder during an expulsion of fluids, and also showing an over center latch pressing the syringe holder to the housing in the engaged position.

Referring briefly to FIG. 25, the syringe holder 320, supported by the pump housing, may include opposed upwardly extending front wall 316 and rear wall 318 forming a channel 319 therebetween receiving and flanking the guide 315 of the shaft collar 314 therein.

Figures 23A, 23B, 24:
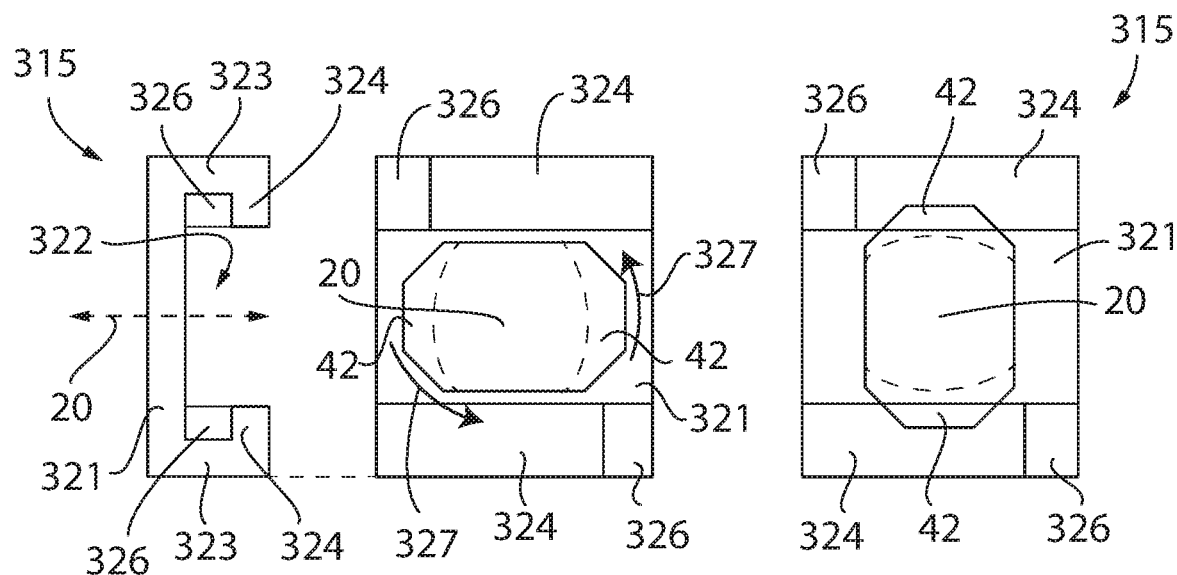
FIGS. 23a-23b are top elevation (FIG. 23a) and side elevation (FIG. 23b) views of a syringe holder receiving the collar ears of the syringe tube.
FIG. 24 is a side elevation view of the syringe holder wherein the syringe holder locks the collar ears of the syringe tube with rotation of the syringe tube.

Referring now to FIG. 23a-23b, the guide 315 of the shaft collar 314 may include opposed upwardly extending rear wall 321 having forwarding extending arms 323 at its outer ends forming a channel 322 having a C-shaped cross-section with inwardly extending wedge surfaces 324 at the opposed ends of the arms 233 whereby the channel 322 allows for the secure insertion of the oppositely extending collar ears 42 into the channel 322. For example, when the collar ears 42 are displaced 90 degrees from the opposed wedge surfaces 324, the collar ears 42 may be inserted into the channel 322, as shown in FIG. 21b.

Referring to FIG. 22, when the collar ears 42 are rotated a quarter turn in a locking direction 327 about axis 20, the collar ears 42 are "locked" or compressed beneath the wedge surfaces 324 to provide a releasable yet secure connection. Stop walls 326 at alternate ends of the wedge surfaces 324, enclosing an open end of the channel 322 between the wedge surface 324, rear wall 321 and arms 323, prevent further rotation of the collar ears 42 beyond a quarter turn in the locking direction 327 within the syringe holder 320 such that the collar ears 42 are maintained in a position compressed by the wedge surfaces 324 and can only be released by a rotation of the collar ears 42 in an opposite direction as the locking direction 327.

The locking direction 327 may be either a clockwise or counterclockwise rotation of the syringe tube 22 to lock the collar ears 42 beneath the wedge surfaces 324 and may correspond with (be the same rotation direction as) the direction of rotation of the twist lock 302 necessary to lock the plunger shaft 24 to the plunger piston 26. In this respect, the corresponding locking direction 327 prevents loosening of the attachment of the plunger shaft 24 and plunger piston 26 during attachment of the syringe unit 12 to the pump housing 300.

Referring to FIG. 25, the front walls 316 of the guide 315 prevent forward movement of the syringe tube 22 along axis 20 and the rear walls 318 of the channel 322 of the guide 315 prevent rearward motion of the syringe tube 22 along axis 20 in order to stabilize the syringe tube 22 during the administration of fluids by the plunger shaft 24 and a plunger piston 26.

Similarly, the front walls 316 of the syringe holder 320 prevent forward movement of the syringe tube 22 along axis 20, and an interior surface 332 of the front walls 316 may support at least one pressure sensor 334 sensing a pressure applied to the interior surface 332 and sending a pressure signal to the internal controller microcontroller 56 indicating an increase in pressure to the front walls 316 indicating a possible occlusion in the IV line. For example, the pressure sensor may be a membrane sensor, strain gauge or piezoelectric sensor. The pressure sensor 334 may electrically communicate with the controller microcontroller 56, for example, containing a microcontroller and memory holding programming discussed with the first and second embodiments, to provide an alert indicating the possible occlusion.

Figure 26:
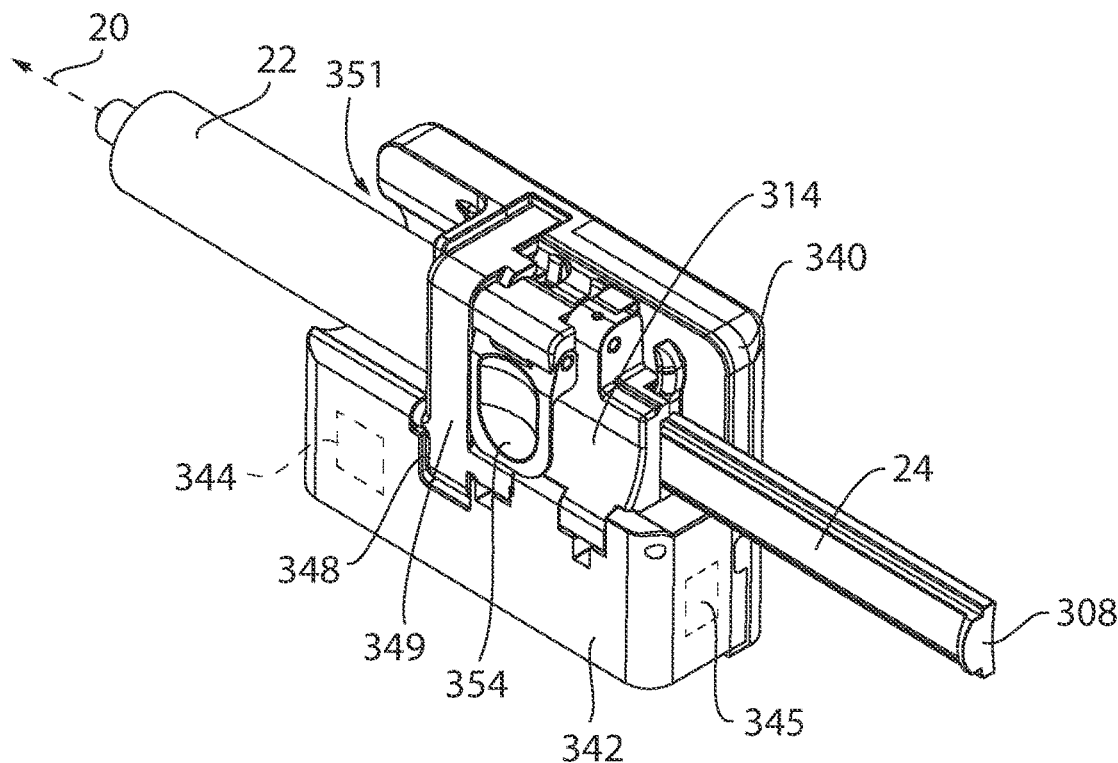
FIG. 26 is a perspective view of a rear side of the syringe holder of FIG. 19 where the syringe holder is pivoted to an engaged position with respect to the housing.

Referring to FIGS. 26 and 27, the pump housing 300 may support the syringe holder 320 whereby the syringe holder 320 may pivot between an engaged (FIG. 26) and a disengaged position (FIG. 27) to couple the syringe unit 12 with the pump elements in the engaged position and to disengage the syringe unit 12 with the pump elements to allow for loading and unloading in the disengaged position. It is understood that the syringe holder 320 generally supports the syringe unit 12 in the pump housing 300 in a manner which allows for an engagement of the pump elements with the syringe unit 12.

The pump housing 300 may include a front enclosure 340 having a rearwardly extending base 342 extending from a lower end of the front enclosure 340 and supporting the syringe holder 320 thereon in pivoting motion upwards and downwards with respect to a rear side of the front enclosure 340. The syringe holder 320 may pivot about an axis of rotation extending along axis 20 and defined by a hinge 348 located below the syringe holder 320. The syringe holder 320 may be supported by a cover element 349 held by the hinge 348.

The base 342 of the pump housing 300 may be a rectangular enclosure supporting therein the motor unit 120 such as a stepper motor 52 connected to and communicating with a gear train 50 translating mechanical energy to a pinion gear 48 supported at a rear side of the front enclosure 340 and engaging the rack 46 of the plunger shaft 24 to expel fluid front the syringe tube 22. The base 342 may also support a self-contained power source such as a battery 344.

The front enclosure 340 of the pump housing 300 may support a controller microcontroller 56, for example, containing a microcontroller and memory holding programming, and communicating with the display screen 58 and input buttons 60, battery 344 and the stepper motor 52 to control, for example, dose, flow rate, timing and the like as described with respect to the first and second embodiments. The controller microcontroller 56 may also communicate with a capacitive sensor 343 discussed above with respect to the first and second embodiments, or alternative sensors also discussed above including optical sensing, magnetic sensing, and the like known for linear displacement measurements.

The front enclosure 340 may further support a near field RFID reader 345 that can read patient, drug or authorization information from RFID tags on the syringe and/or from a tag associated with the medical professional administering the drug, and configure the pump for infusion and/or authorize the medical professional to administer the drug protocol. The front enclosure 340 may also support a sensing switch 347 that detects the engagement of the syringe unit 12 with the front enclosure 340 in a manner which initiates on-off operation of the pump and motor.

Referring to FIG. 27, in the disengaged position, the syringe holder 320 is pivoted downwards, via the cover element 349, away from the pump housing 300 with an insertion opening of the channel 319 of the syringe holder 320 opening upwards allowing for the insertion of the guide 315 downwards into the channel 319 along an insertion axis 346 perpendicular to the axis 20. Similarly, the channel 322 of the guide 315 opens upwards allowing for the insertion of the collar ears 42 of the syringe tube 22 downwards into the channel 322 along the insertion axis 346.

Once the collar ears 42 of the syringe tube 22 are inserted into the channel 322, the collar ears 42 generally positioned along the axis 346, the syringe tube 22 may be rotated about a quarter turn in the locking direction 327 to lock the syringe tube 22 into the guide 315. Upon the insertion of the collar ears 42 into the guide 315, the twist lock 302 of the plunger shaft 24 and the plunger piston 26 may be engaged to lock the plunger shaft 24 and the plunger piston 26 together with rotation of the syringe tube 22 in the common locking direction 327. In this respect, the locking of the syringe tube 22 to the pump housing 300 and of the plunger piston 26 and the plunger shaft 24 may be simultaneous with a quarter turn twisting action. Once the syringe unit 12 is coupled to the pump syringe holder 320, the syringe holder 320 may be rotated upward to the engaged position.

Referring to FIG. 26, in the engaged position, the syringe holder 320 may be pivoted upwards, via the cover element 349, towards the rear side of the front enclosure 340 of the pump housing 300. In this position, the insertion opening of the channel 319 of the syringe holder 320 opens toward the rear side of the front enclosure 340 but is enclosed by the abutment of the rear side wall. The front enclosure 340 may include a circular cut out 351 proximate the syringe tube 22 to accommodate the cylindrical body of the syringe tube 22 in close abutment with the rear side of the front enclosure 340 which allows the pinion gear 48 of the rear side of the front enclosure 340 to engage the rack 46 to initiate direct drive delivery of the drug. In this respect, the opening 313 of the shaft collar 314 is aligned with the position of the pinion gear 48 to allow for the proper alignment of the rack 46 with the pinion gear 48 in the engaged position.

Referring again to FIG. 25, the syringe holder 320 may lock to the front enclosure 340 of the pump housing 300 by a latch having a hook 350 extending toward the front enclosure 340 to engage a rod 352 of the rear side of the front enclosure 340 and secured by an over center latch 354 which pivots about hinge 356 and locks the hook 350 to the rod 352 with closure of the latch 354 downward away from the front enclosure 340, as understood in the art.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

We claim:

1. A syringe for delivery of a liquid medicament, the syringe comprising:
a tubular barrel extending along an axis from an open end to a needle adapter, the open end having outwardly extending grip flanges;
a plunger having a first end fitting within the tubular barrel to move along the axis within the tubular barrel;
a first connector attached to the first end of the plunger;
an elastomeric piston sealingly fitting within the tubular barrel and movable along the axis within the tubular barrel; and
a second connector attached to the elastomeric piston and connectable to the first connector to resist separation of the first connector and second connector along the axis;
wherein the second connector has a cantilevered arm supporting an inwardly extending tooth flexibly engaging with an outwardly facing groove of the first connector;
wherein the inwardly extending tooth of the second connector is insertable into the outwardly facing groove of the first connector along a circular path encircling the axis with a relative rotation of the first connector with respect to the second connector about the axis;
wherein the inwardly cantilevered arm extends in cantilever traverse to the axis along the circular path to be fixed along the circular path at a first end and unfixed along the circular path at a second end to deflect the inwardly extending tooth away from the circular path in a direction radial to the axis;
wherein the first connector has an outwardly extending pin engaging with a slot of the second connector and the slot of the second connector extends along the circular path between the cantilevered arm and the elastomeric piston.

2. The syringe of claim 1 wherein the first and second connector provide a predetermined axial separation between the first end of the plunger and a face of the elastomeric piston.

3. The syringe of claim 1 further comprising a shaft collar supporting linear translation of the plunger through the shaft collar along the axis and supporting outwardly extending finger grips.

4. The syringe of claim 3 wherein the shaft collar further supports a guide extending perpendicular to the axis providing opposed walls with inwardly facing channels removably receiving the grip flanges of the tubular barrel.

5. The syringe of claim 4 wherein the grip flanges of the barrel are secured into the shaft collar by twisting the barrel in the first direction thereby rotating the grip flanges to fit between the channels.

6. The syringe of claim 4 further comprising a holder extending perpendicular to the axis providing opposed walls removably receiving the shaft collar.

7. The syringe of claim 6 further comprising a housing supporting the holder on a pivotable cover, pivotable to a base supporting a motor unit attached to and stationary with respect to the housing and engaging the plunger to move the plunger with motion of the motor unit.

8. The syringe of claim 6 further comprising a housing supporting the holder on a pivotable cover, pivotable to a base supporting an electronic sensor attached to and stationary with respect to the base and sensing a sensor element of the syringe to provide direct measurement of motion of the plunger along the axis with respect to the housing to provide an electronic signal indicating movement of the plunger.

9. The syringe of claim 8 wherein a latch compresses the pivotable cover against the base to align the plunger with the motor.

10. The syringe of claim 6 further comprising an electronic sensor attached to at least one of a front and rear wall of the holder and sensing a pressure applied to the front and rear wall to provide an indication of increased pressure along the axis with respect to the holder to provide an electronic signal indicating an occlusion in the syringe.

11. The syringe of claim 1 wherein the elastomeric piston is free from hollow areas that compress during use.

12. The syringe of claim 11 wherein the elastomeric piston is attached to the second connector at respective attachment ends and at least one of the elastomeric piston and the second connector fills a space within the other of the elastomeric piston and the second connector at the attachment ends.

13. The syringe of claim 12 wherein the space is filled with a plastic material.

14. The syringe of claim 1 wherein the relative rotation of the first connector with respect to the second connector is stopped from further rotation by a positive stop.

15. A syringe for delivery of a liquid medicament, the syringe comprising:
   a tubular barrel extending along an axis from an open end to a needle adapter, the open end having outwardly extending grip flanges;
   a plunger having a first end fitting within the tubular barrel to move along the axis within the tubular barrel;
   a first connector attached to the first end of the plunger;
   an elastomeric piston sealingly fitting within the tubular barrel and movable along the axis within the tubular barrel; and
   a second connector attached to the elastomeric piston and connectable to the first connector to resist separation of the first connector and second connector along the axis;
   wherein the elastomeric piston is free from hollow areas that compress during use;
   wherein one of the first and second connector has a cantilevered arm supporting a tooth flexibly engaging with a groove of the other of the first and second connector
   wherein the tooth of the second connector is insertable into the groove of the first connector along a circular path encircling the axis with a relative rotation of the first connector with respect to the second connector about the axis wherein the cantilevered arm extends in cantilever traverse to the axis along the circular path to be fixed along the circular path at a first end and unfixed along the circular path at a second end to deflect the cantilevered tooth away from the circular path in a direction radial to the axis
   wherein the first connector has an outwardly extending pin engaging with a slot of the second connector and the slot of the second connector extends along the circular path between the cantilevered arm and the elastomeric piston.

16. The syringe of claim 15 wherein the elastomeric piston is attached to the second connector at respective attachment ends and at least one of the elastomeric piston and the second connector fills a space within the other of the elastomeric piston and the second connector at the attachment ends.

17. The syringe of claim 16 wherein the space is filled with a plastic material.

* * * * *